(12) United States Patent
Belur Nagaraj et al.

(10) Patent No.: US 12,076,159 B2
(45) Date of Patent: Sep. 3, 2024

(54) COMBINING MULTIPLE QEEG FEATURES TO ESTIMATE DRUG-INDEPENDENT SEDATION LEVEL USING MACHINE LEARNING

(71) Applicant: Masimo Corporation, Irvine, CA (US)

(72) Inventors: Sunil Belur Nagaraj, Groningen (NL); Sowmya Muchukunte Ramaswamy, Groningen (NL); Michel Maria R. Struys, Belsele (BE)

(73) Assignee: Masimo Corporation, Irvine, CA (US)

( * ) Notice: Subject to any disclaimer, the term of this patent is extended or adjusted under 35 U.S.C. 154(b) by 618 days.

(21) Appl. No.: 16/784,067

(22) Filed: Feb. 6, 2020

(65) Prior Publication Data
US 2020/0253544 A1    Aug. 13, 2020

Related U.S. Application Data

(60) Provisional application No. 62/847,824, filed on May 14, 2019, provisional application No. 62/802,575, filed on Feb. 7, 2019.

(51) Int. Cl.
*A61B 5/00* (2006.01)
*A61B 5/316* (2021.01)
(Continued)

(52) U.S. Cl.
CPC ............ *A61B 5/4821* (2013.01); *A61B 5/316* (2021.01); *A61B 5/369* (2021.01); *A61B 5/7246* (2013.01);
(Continued)

(58) Field of Classification Search
CPC ... A61B 5/4821; A61B 5/7246; A61B 5/7267; A61B 5/742; G06N 7/005; G06N 20/10; G06N 20/20; G16H 20/17
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |

(Continued)

FOREIGN PATENT DOCUMENTS

| | | | |
|---|---|---|---|
| CN | 109222950 | * | 1/2019 |
| WO | WO 2012/154701 | | 11/2012 |
| WO | WO 2020/163640 | | 8/2020 |

OTHER PUBLICATIONS

US 2022/0192529 A1, 06/2022, Al-Ali et al. (withdrawn)
(Continued)

*Primary Examiner* — David J. McCrosky
*Assistant Examiner* — Clarissa Cuevas
(74) *Attorney, Agent, or Firm* — Knobbe, Martens, Olson & Bear, LLP

(57) ABSTRACT

The present disclosure describes systems and methods of estimating sedation level of a patient using machine learning. For example, the integration of multiple QEEG features into a single sedation level estimation system using machine learning could result in a significant improvement in the predictability of the levels of sedation, independent of the sedative drug used. The present disclosure advantageously allows for the incorporation of large numbers of QEEG features and machine learning into the next-generation monitors of sedation level. Different QEEG features may be selected for different sedation drugs, such as propofol, sevoflurane and dexmedetomidine groups. The sedation level estimation system can maintain a high performance for detecting MOAA/S, independent of the drug used.

8 Claims, 14 Drawing Sheets

(51) Int. Cl.
  *A61B 5/369* (2021.01)
  *G06N 7/01* (2023.01)
  *G06N 20/10* (2019.01)
  *G06N 20/20* (2019.01)
  *G16H 20/17* (2018.01)

(52) U.S. Cl.
  CPC ............ *A61B 5/7267* (2013.01); *A61B 5/742* (2013.01); *G06N 7/01* (2023.01); *G06N 20/20* (2019.01); *G16H 20/17* (2018.01)

(56) References Cited

U.S. PATENT DOCUMENTS

| | | | |
|---|---|---|---|
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,890,929 A | 4/1999 | Mills et al. | |
| 5,919,134 A | 7/1999 | Diab | |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,232,609 B1 | 5/2001 | Snyder et al. | |
| 6,241,683 B1 | 6/2001 | Macklem et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,360,114 B1 | 3/2002 | Diab et al. | |
| 6,368,283 B1 | 4/2002 | Xu et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,658,276 B2 | 12/2003 | Kiani et al. | |
| 6,661,161 B1 | 12/2003 | Lanzo et al. | |
| 6,697,656 B1 | 2/2004 | Al-Ali | |
| 6,697,658 B2 | 2/2004 | Al-Ali | |
| RE38,476 E | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| 6,920,345 B2 | 7/2005 | Al-Ali et al. | |
| 6,934,570 B2 | 8/2005 | Kiani et al. | |
| 6,943,348 B1 | 9/2005 | Coffin IV | |
| 6,956,649 B2 | 10/2005 | Acosta et al. | |
| 6,961,598 B2 | 11/2005 | Diab | |
| 6,970,792 B1 | 11/2005 | Diab | |
| 6,985,764 B2 | 1/2006 | Mason et al. | |
| 6,990,364 B2 | 1/2006 | Ruchti et al. | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,225,006 B2 | 5/2007 | Al-Ali et al. | |
| RE39,672 E | 6/2007 | Shehada et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,356,365 B2 | 4/2008 | Schurman | |
| 7,371,981 B2 | 5/2008 | Abdul-Hafiz | |
| 7,373,193 B2 | 5/2008 | Al-Ali et al. | |
| 7,377,794 B2 | 5/2008 | Al-Ali et al. | |
| 7,395,158 B2 | 7/2008 | Monfre et al. | |
| 7,415,297 B2 | 8/2008 | Al-Ali et al. | |
| 7,438,683 B2 | 10/2008 | Al-Ali et al. | |
| 7,483,729 B2 | 1/2009 | Al-Ali et al. | |
| D587,657 S | 3/2009 | Al-Ali et al. | |
| 7,500,950 B2 | 3/2009 | Al-Ali et al. | |
| 7,509,494 B2 | 3/2009 | Al-Ali | |
| 7,510,849 B2 | 3/2009 | Schurman et al. | |
| 7,514,725 B2 | 4/2009 | Wojtczuk et al. | |
| 7,519,406 B2 | 4/2009 | Blank et al. | |
| D592,507 S | 5/2009 | Wachman et al. | |

(56) References Cited

U.S. PATENT DOCUMENTS

| | | |
|---|---|---|
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |

(56) References Cited

U.S. PATENT DOCUMENTS

| | | |
|---|---|---|
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| 9,986,952 B2 | 6/2018 | Dalvi et al. |
| D820,865 S | 6/2018 | Muhsin et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |

(56) References Cited

U.S. PATENT DOCUMENTS

| | | |
|---|---|---|
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2016/0196388 A1 | 7/2016 | Lamego |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0353084 A1* | 12/2018 | Wainright ............... A61B 8/00 |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |

(56) References Cited

U.S. PATENT DOCUMENTS

| | | |
|---|---|---|
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |

OTHER PUBLICATIONS

US 2024/0016391 A1, 01/2024, Lapotko et al. (withdrawn)
Levy WJ. Effect of epoch length on power spectrum analysis of the EEG. Anesthesiology. Apr. 1987;66(4):489-95. doi: 10.1097/00000542-198704000-00007. PMID: 3565814. (Year: 1987).*
Machine Translation of CN109222950 (Year: 2019).*
Rampil IJ. A primer for EEG signal processing in anesthesia. Anesthesiology. Oct. 1998;89(4):980-1002. doi: 10.1097/00000542-199810000-00023. PMID: 9778016. (Year: 1998).*
Drover et al., "Patient State Index", Best Practice & Research Clinical Anaesthesiology, 2006, vol. 20, No. 1, pp. 121-128.
Greene et al., "Automated Estimation of Sedation Depth from the EEG", 2007 Annual International Conference of the IEEE Engineering in Medicine an Biology Society, Lyon, France, Aug. 22-26, 2007, pp. 3188-3191.
International Search Report and Written Opinion received in International Application No. PCT/US2020/017074, dated Jun. 4, 2020 in 11 pages.
Schmidt et al., "Measurement of the Depth of Anesthesia", Der Anaesthesist, 2008, vol. 57, pp. 9-36.
Letter from Tara A. Ryan to Masimo Corporation re 510(k) No. K172890, U.S. Food & Drug Administration, dated Jan. 26, 2018.
Letter from Todd D. Courtney to Masimo Corporation re 510(k) No. K203133, U.S. Food & Drug Administration, dated Feb. 25, 2022.
Nagaraj et al., "Electroencephalogram Based Detection of Deep Sedation in ICU Patients Using Atomic Decomposition", IEEE Transactions on Biomedical Engineering, Dec. 2018, vol. 65, No. 12, pp. 2684-2691.
Ramaswamy et al., "A Novel Machine Learning based Drug-Independent Sedation Level Estimation using Quantitative Features from the Frontal Electroencephalogram", Manuscript, Clinical trial registration: NCT 02043938, 2019, pp. 36.

* cited by examiner

COMBINING MULTIPLE QEEG FEATURES TO ESTIMATE DRUG-INDEPENDENT SEDATION LEVEL USING MACHINE LEARNING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF DISCLOSURE

The present disclosure relates to the field of patient monitoring. In some examples, the disclosure relates to monitoring the depth of consciousness of a patient under anesthetic sedation.

BACKGROUND OF THE INVENTION

Sedation indicators based on a single quantitative electroencephalogram (QEEG) feature have been criticized for limited performance as estimates of the sedation level of a patient. Thus, an improved way to estimate sedation level may be desirable. There is a need for robust sedation level monitoring systems to accurately track sedation levels across all drug classes, sex, and age groups.

SUMMARY

The present disclosure describes systems and methods for estimating sedation level of a patient using machine learning. For example, the integration of multiple quantitative electroencephalogram (QEEG) features into a single sedation level estimation system 200 using machine learning could result in a significant improvement in the predictability of the levels of sedation, independent of the sedative drug used.

In one example, 102 subjects were studied, with 36 subjects given propofol (N=36), 36 subjects given sevoflurane (N=36), and 30 subjects given dexmedetomidine (N=30). Subject sedation level was assessed using the Modified Observer's Assessment of Alertness/Sedation (MOAA/S) score. Forty four QEEG features estimated from the EEG data were used in a logistic regression based automated system to predict the level of sedation. Elastic-net regularization method was used for feature selection and model training. Evaluation were performed using leave-one-out cross validation methodology. The area under the receiver operator characteristic curve (AUC) and Spearman rank correlation coefficient (p) were used to assess the performance of the logistic regression model. The following performances were obtained when the system was trained and tested as drug dependent mode to distinguish between awake and sedated states (mean AUC±SD): propofol—0.97 (0.03), sevoflurane—0.74 (0.25), and dexmedetomidine—0.77 (0.10). The drug independent system resulted in a mean AUC=0.83 (0.17) to discriminate between awake and sedated states, and mean Spearman rank correlation $\rho$=0.54 (0.21) to predict continuous levels of sedation.

The present disclosure advantageously allows for the incorporation of large numbers of QEEG features and machine learning into the next-generation monitors of sedation level. Different QEEG features may be selected for different sedation drugs, such as propofol, sevoflurane and dexmedetomidine groups. However, the sedation level estimation system can maintain a high performance for detecting level of sedation, independent of the drug used.

In some embodiments, disclosed herein is a method for generating a sedation level estimate. The method can include receiving an electroencephalography (EEG) signal from a sensor electrode attached to the patient. The EEG can include a plurality of channels. The method can further include segmenting the EEG signal into smaller epochs for each channel. The method can also include extracting features of the EEG signal in each epoch. The method can further include determining a median of features among the plurality of channels for each epoch. In some instances, the method can include determining, by a classifier, a probabilistic estimate of a patient sedation. The method can also include generating, using a determined correlation, a sedation level estimate, the sedation level estimate comprising a continuous sedation score. In some instances, the method can include displaying an indication of the sedation level estimate. The method can be performed by one or more hardware processors.

In some instances of the preceding method, the epoch can be 4 seconds. In some instances, the features include quantitative electroencephalogram (QEEG) features. In some instances, extracting features include extracting at least 44 QEEG features. In some instances, extracting features include extracting at least some of the 44 QEEG features. In some instances, the classifier includes a binary classifier trained by a machine learning model. Further, in some instances, the binary classifier is trained using awake and sedated epoch data, the awake and sedated epoch data can include a plurality of epochs having sedation scores. The sedation scores can include a score on a scale of 0 to 5. The sedation scores can also include a score between 0 and 100. The sedation scores can also include MOAA/S scores. Furthermore, the determined correlation can include a correlation between the probabilistic estimate of the patient sedation and a sedation score. In some instances, the determined correlation include a spearman rank-correlation.

In some embodiments, disclosed herein is a system for generating a sedation level estimate. The system can include one or more hardware processors. The one or more hardware processors can receive an electroencephalography (EEG) signal from a sensor electrode attached to the patient. The EEG can include a plurality of channels. The one or more hardware processors can segment the EEG signal into smaller epochs for each channel. The one or more hardware processors can extract features of the EEG signal in each epoch. The one or more hardware processors can determine a median of features among the plurality of channels for each epoch. In some instances, the one or more hardware processors can determine, by a classifier, a probabilistic estimate of a patient sedation. The one or more hardware processors can also generate, using the determined correlation, a sedation level estimate, the sedation level estimate including a continuous sedation score. In some instances, the one or more hardware processors can cause a display to display an indication of the sedation level estimate.

In some instances of the preceding system, the epoch can be 4 seconds. In some instances, the features include quantitative electroencephalogram (QEEG) features. In some instances, extracting features include extracting at least 44 QEEG features. In some instances, extracting features include extracting at least some of the 44 QEEG features. In some instances, the classifier includes a binary classifier trained by a machine learning model. Further, in some instances, the binary classifier is trained using awake and sedated epoch data, the awake and sedated epoch data can include a plurality of epochs having sedation scores. The sedation scores can include a score on a scale of 0 to 5. The sedation scores can also include a score between 0 and 100. The sedation scores can also include MOAA/S scores. Furthermore, the determined correlation can include a correlation between the probabilistic estimate of the patient sedation and a sedation score. In some instances, the determined correlation include a spearman rank-correlation.

In some embodiments, disclosed herein is a method of selecting a subset of EEG features for use in an electronic determination of sedation state across a plurality of drugs. The method can include receiving EEG signal data from an EEG sensor for a plurality of administered drugs. The method can also include associating a human determined sedation score corresponding to patient's sedation state with the received EEG signal data. The method can further include selecting EEG signals with the associated human determined sedation score that has a high degree of confidence. The method can also include extracting a plurality of features from the selected EEG signals. The method can further include training the plurality of features with the corresponding human determined sedation scores. In some instances, the method can include identifying a set of features with a high degree of correlation based on the training.

In some embodiments, disclosed herein is a system of selecting a subset of EEG features for use in an electronic determination of sedation state across a plurality of drugs. The system can include one or more hardware processors. The one or more hardware processors can receive EEG signal data from an EEG sensor for a plurality of administered drugs. The one or more hardware processors can associate a human determined sedation score corresponding to patient's sedation state with the received EEG signal data. The one or more hardware processors can select EEG signals with the associated human determined sedation score that has a high degree of confidence. The one or more hardware processors can extract a plurality of features from the selected EEG signals. The one or more hardware processors can further train the plurality of features with the corresponding human determined sedation scores. In some instances, the one or more hardware processors can identify a set of features with a high degree of correlation based on the training.

In some embodiments, disclosed herein is a method of determining sedation state of a patient. The method can include receiving EEG signal data from an EEG sensor. The method can further include extracting features from the received EEG signal data. The method can also include applying non-linear machine learning model to the received EEG signal data. The method can also include determining the sedation state based on the application of the non-linear machine learning model.

The preceding method can include any combination of the following features, wherein the non-linear machine learning model includes ensemble tree with bagging model; wherein the non-linear machine learning model includes random forest model; wherein the non-linear machine learning model includes support vector machine with Gaussian kernel model; wherein the non-learning model comprises elastic net logistic regression; wherein the features include at least power in alpha band and power in beta band; wherein the features include at least BSR, standard deviation of FM, SVDE and FD.

In some embodiments, disclosed herein is a system of determining sedation state of a patient. The system can include one or more hardware processors. The one or more hardware processors can receive EEG signal data from an EEG sensor. The one or more hardware processors can extract features from the received EEG signal data. The one or more hardware processors can apply non-linear machine learning model to the received EEG signal data. The one or more hardware processors can determine the sedation state based on the application of the non-linear machine learning model.

The preceding system can include any combination of the following features, wherein the non-linear machine learning model includes ensemble tree with bagging model; wherein the non-linear machine learning model includes random forest model; wherein the non-linear machine learning model includes support vector machine with Gaussian kernel model; wherein the non-learning model comprises elastic net logistic regression; wherein the features include at least power in alpha band and power in beta band; wherein the features include at least BSR, standard deviation of FM, SVDE and FD.

DETAILED DESCRIPTION

A. Introduction

Figure 1A:
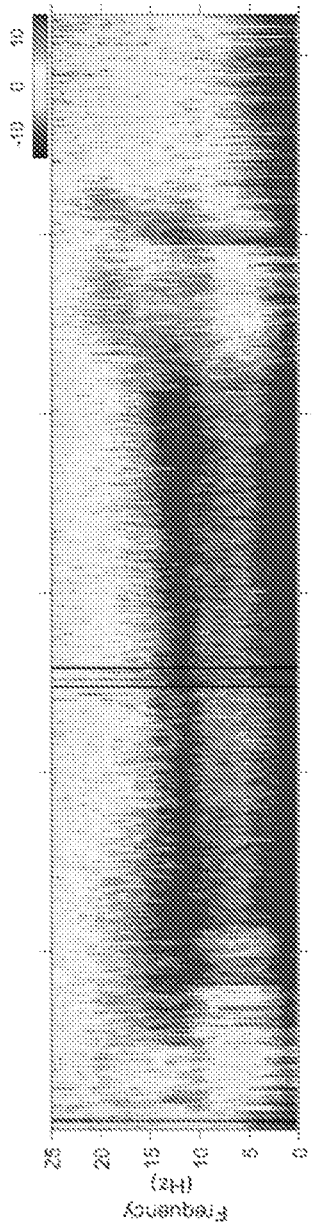
FIG. 1A illustrates an example Frontal EEG spectrogram of a volunteer in the propofol group.

Optimal management of the level of sedation becomes increasingly important during surgical procedures to ensure minimal side effects and rapid recovery of the patient. Current practice for monitoring the sedation state during anesthesia relies mainly on the behavioral assessments of the patients' response to a verbal and/or tactile stimulus. However, these behavioral assessments can only be performed intermittently by the anesthesiologist. Moreover, it may be difficult to quantify sedative effect once all visible responsiveness of the patient to verbal, tactile or noxious stimuli have disappeared. Without the availability of continuous information on the sedation level, anesthetic drug administration can result in over or under dosage, leading to a variety of complications. For the past few decades developing electroencephalogram (EEG) based sedation level monitoring techniques has been an active area of research and many such techniques have been developed. However, their performance is limited due to drug specificity and inter- (and intra-) subject variability. Neurophysiological distinctions, age and sex-dependent EEG changes between sedation drugs highlight the need for more robust techniques to monitor sedation levels or patient sedation index.

Anesthetic-induced oscillatory dynamics (e.g., time-varying amplitude and frequency characteristics) are readily observed on the EEG, and can be used to monitor patients receiving general anesthesia in real time. Each anesthetic drug class induces drug-specific oscillatory dynamics that can be related to circuit level mechanisms of anesthetic actions. Further, anesthetic induced oscillatory dynamics change with age. Thus, a EEG based sedation level monitoring system should be robust with drug and/or age specific variations.

Different sedatives produce specific EEG signatures. An important design factor in any sedation monitoring algorithms is the choice of relevant features to extract from the EEG signal. The present disclosure relates to a machine learning based drug-independent sedation level monitoring system and sedation level estimate using a large set of QEEG features. In some examples, several features derived from the frontal EEG, commonly reported for EEG and sedation level analysis, can be used as input to a logistic regression for automatically predicting a patient's sedation level. Furthermore, the systems and methods described herein can enable determination of a specific set of features from the larger set that are suitable for particular conditions—including patient characteristics and drug characteristics. For example, the systems and methods described herein enable feature selection to be used in determination of sedation for a particular group of drugs. Furthermore, once the features are selected, the systems and methods described herein can store the features and corresponding weights that enable determination of level of sedation.

B. Overview

This disclosure describes systems and methods for a machine learning-based automatic drug independent sedation level estimation system 200. The sedation level estimation system 200 can use a large set of QEEG features to generate a sedation level estimate. Example QEEG features are described below. The set of QEEG features can include features that may capture EEG dynamics in time, frequency and entropy domains. The set of QEEG features may be derived from frontal EEG. The level estimation system 200 can be based on probability output of the logistic regression evaluated on healthy subjects during anesthesia with propofol (N=36), sevoflurane (N=36) and dexmedetodimine (N=30) infusion. The model can be assessed using AUC as a metric. In one example, the level estimation system 200 resulted in a mean AUC=0.97 (0.03), 0.74 (0.25), 0.77 (0.10) for propofol, sevoflurane and dexmedetomidine, respectively, to discriminate between awake and sedated states in drug dependent mode. In another example, the sedation level estimation system 200, when used in a drug independent mode, resulted in an overall mean AUC=0.83 (0.17). Thus, by pooling the dataset from multiple anesthetic drugs, it is possible to obtain a reliable sedation level estimation system 200 with the help of machine learning algorithms.

The systems and methods disclosed take a multidimensional approach using machine learning techniques and a large set of QEEG features to predict levels of sedation. The performance of the sedation level estimation system 200 can depend on the type of anesthetic drug used for training the classifier model. For example, different features can be selected by the prediction system for propofol, sevoflurane and dexmedetomidine. This may be due to different anesthetics targeting different molecules and engaging different neural circuit mechanisms, which in turn relate to different drug-specific EEG signatures.

An ideal sedation level estimate should be easy to interpret and should not be influenced by the type of anesthetics used. With the help of large set of QEEG features and machine learning algorithms, it is possible to develop a drug independent sedation level estimation system 200. To implement the disclosed system in clinical settings, features selected by an EN algorithm on the training set can help predict sedation levels on the new subject. For a new patient, for each 4 second incoming EEG signal, the system may estimate only those features selected by the EN algorithm and input those features into the optimal model to predict the probability of being in a sedated state.

In some examples, the performance of sedation level estimation system 200 was lower with dexmedetomidine sedation when compared to propofol and sevoflurane. One possible reason is due to the difference in the mechanism of dexmedetomidine-induced sedation from that of propofol and sevoflurane induced sedation. Patients receiving dexmedetomidine can be in a "moderate sedation" state, often remain cooperative and can be awakened/aroused easily. In contrast, propofol and sevoflurane induces the patient in a general anesthetic state, and therefore the machine learning algorithm can easily discriminate between different sedation levels when compared to dexmedetomidine.

The disclosed sedation level estimation system 200 has several advantages: 1) It can be objective, free from human behavioral assessment error, 2) it can provide an approximately continuous probabilistic measure for meaningful clinical interpretation, 3) it can have good time-resolution (in other words, it can provide a sedation level estimate once every 4 s), and 4) it can be used across multiple drugs.

C. Example Measurement of EEG Data

In one example, EEG data for propofol and sevoflurane were recorded using a 16 channel EEG monitor in healthy volunteers with a sampling frequency=5 kHz and were later reduced to 1 kHz during transition to extraction file. In another example, 32 channel EEG data for dexmedetomidone was recorded using an amplifier with a recorder at a sampling rate of 5 kHz. In some examples, subjects were asked to keep their eyes closed for the entire study duration. Subjects can be excluded in cases of body weight being less than 70% or more than 130% of ideal body weight, pregnancy, neurological disorder, diseases involving the cardiovascular, pulmonary, gastric, and endocrinological system, or recent use of psycho-active medication or intake of more than 20 g of alcohol daily. The collection and processing of EEG data can be performed by the controller 1400 as discussed in more detail with respect to FIG. 14.

D. Example Methods of Drug Administration

Propofol can be administered through an intravenous line. The pharmacokinetic-dynamic (PKPD) model of Schnider can be used to predict the effect-site concentration (CePROP). After 2 minutes of baseline measurements, a "staircase" step-up and step-down infusion of propofol can be administered. For example, the initial CePROP can be set to 0.5 μg mL$^{-1}$ followed by successive steps toward target concentration of 1, 1.5, 2.5, 3.5, 4.5, 6 and 7.5 μg mL$^{-1}$.

Sevoflurane can be titrated to target or maintain an approximately constant end-tidal sevoflurane (ETSEVO). For example, the initial ETSEVO can be set to 0.2 vol % followed by successive ETSEVO of 0.5, 1, 1.5, 2.5, 3.5, 4, 4.5 vol %. The upwards staircase can be followed until tolerance/no motoric response to all stimuli is observed and a significant burst suppression ratio of at least 40% is attained (for both propofol and sevoflurane). Next, the downward staircase steps can be initiated, using identical targets but in reverse order. In order to obtain a pharmacological steady state at each new step in drug titration, a 12 minutes equilibration time can be maintained once the desired predicted effect-site concentration of propofol or the measured end-tidal vol % of sevoflurane was reached.

Dexmedetomidine can be delivered by using effect site target controlled infusion. Before dexmedetomidine is administered, and after checking adequate function of all monitors, a 5 minutes baseline measurement can be performed during which the volunteer is asked not to talk, to close the eyes and relax for some minutes. After gathering initial baseline data, dexmedetomidine infusion can be initiated, with the following targeted effect site concentrations: 1.0 ng/ml (0-40 mins), 3.0 ng/ml (40-90 mins), 4.0 ng/ml (90-130 mins), 5.0 ng/ml (130-170 mins), and 6.0 ng/ml (170-200 mins). Adventageously, this protocol can allow all effect sites to reach an approximately steady state. Fifty minutes after increasing to a concentration of 6.0 ng/ml, dexmedetomidine infusion can be ceased.

E. Sedation Assessment

Figure 1B:
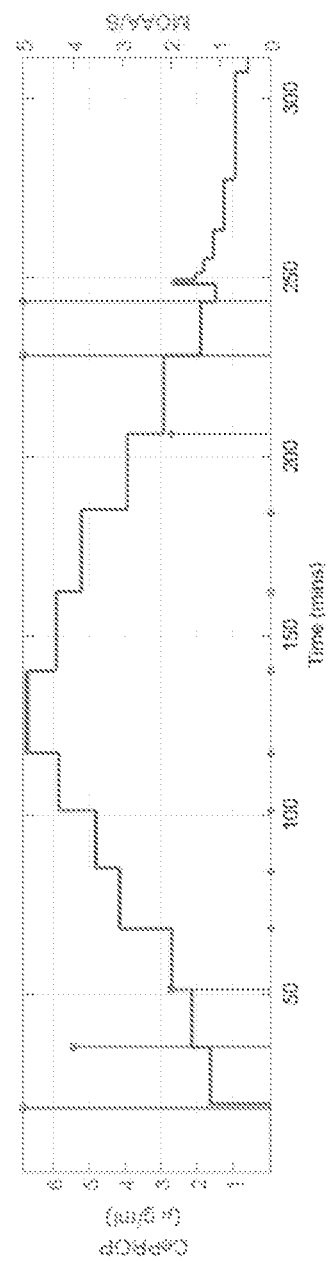
FIG. 1B illustrates an example propofol blood concentration level (BCL), and corresponding Modified Observer's Assessment of Alertness/Sedation Scale (MOAA/S). CePROP corresponds to example targeted propofol effect-site concentrations.

The Modified Observer's Assessment of Alertness/Sedation (MOAA/S) score can be used to score patient sedation levels. MOAA/S scores can range from 5 (responsive to auditory stimuli) to 0 (deeply sedated/unresponsive/comatose). In some examples, the performance of the disclosed system was tested to discriminate between two MOAA/S groups that are clearly well distinguishable from a clinical viewpoint in terms of patient's level of consciousness: awake [MOAA/S 5 and 4] versus sedated [MOAA/S 1 and 0]. An example illustrating the behavioural response and its corresponding EEG spectrogram for an example propofol induced subject is shown in FIGS. 1A and 1B.

F. Example Sedation Level Estimation System

Figure 14:
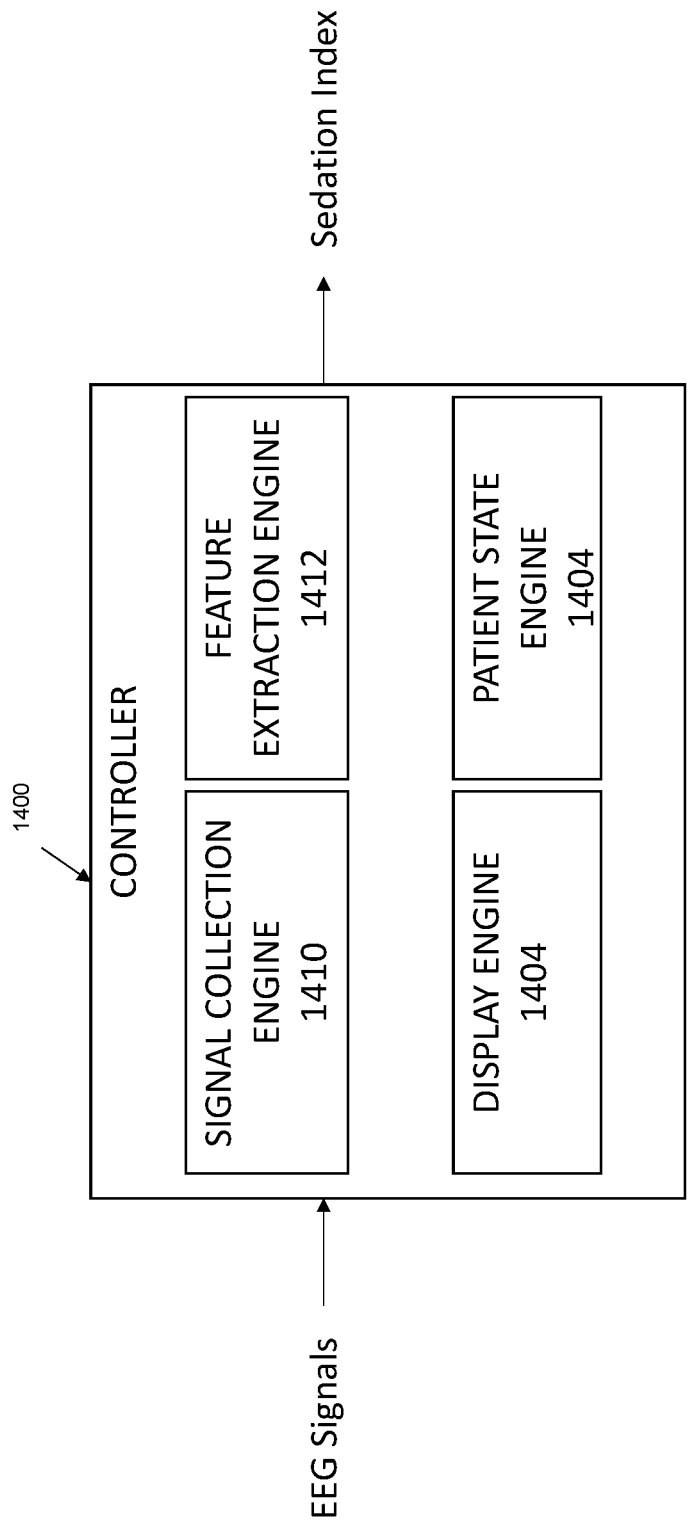
FIG. 14 illustrates a block diagram of a controller for processing and analyzing EEG signals to determine state of sedation.

A sedation level estimation system 200 can include a number of processes implemented by a controller 1400 as discussed with respect to FIG. 14. The controller 1400 can include one or more engines for processing, analyzing, and transforming the non-invasive sensor signals into output(s) that are readable by a clinician. The engines and other aspects of the controller 1400 can include programmed instructions capable of being executed on one or more hardware processors. The programmed instructions can be stored in a memory. The programmed instructions can correspond to the processes described herein. The engines and other aspects of the controller 1400 may also be implemented in a combination of hardware, such as circuits, FPGA, ASICs and the like and programmed instructions. The controller 1400 may operate the engines in parallel on the one or more hardware processors.

In one example, the controller 1400 may perform the preprocessing step signals from EEG channels and segmenting them into short duration epochs. Several QEEG features can be extracted from each EEG epoch and combined by taking the median across channels. The feature vectors can then be fed to the classifier and the probability of each sedation level can be obtained for each EEG epoch. An automated probabilistic sedation level estimate can then obtained. The architecture can be implemented as programmed instructions executed by one or more hardware processors. The architecture can be implemented with Masimo Sedline® Brain Function Monitor (sold by Masimo of Irvine, CA). An example architecture is described in more specificity with respect to FIGS. 12 and 13 below.

In some examples, four frontal EEG channels arranged in bipolar configuration may be used to collect EEG signals. For example, EEG signals from Fp1, Fp2, F7, and F8 electrodes in a Fp1-F7 and Fp2-F8 configuration may be used. However, other configurations of EEG electrodes may be used.

Figure 2:
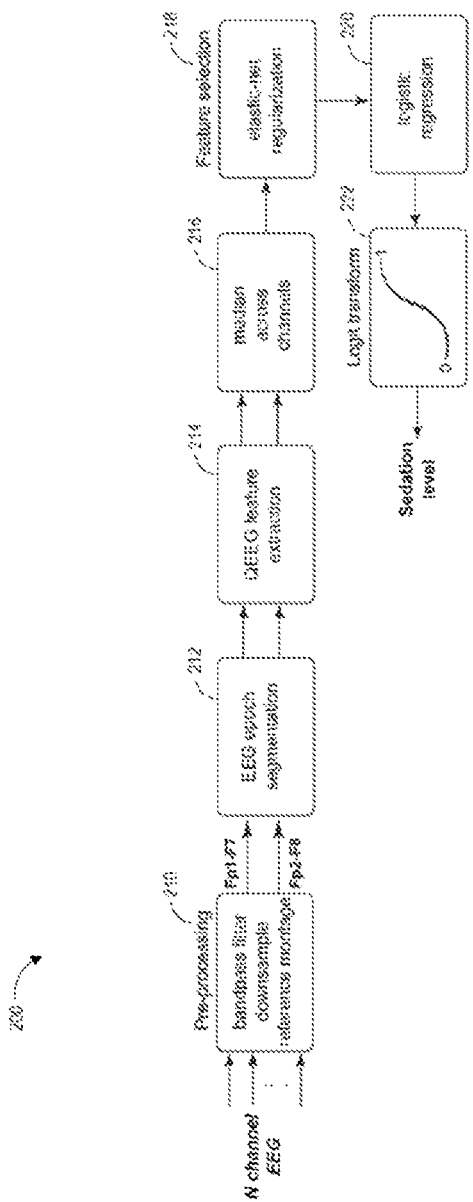
FIG. 2 illustrates an example architecture of one example of the sedation level estimation system.

As shown in FIG. 2, a sedation level estimation system 200 can include a preprocessor block 210, an EEG epoch segmentation block 212, a feature extraction block 214, a median block 216, a feature selection block 218, a logistic regression block 220, and a discrete to continuous (DTC) transform block 222. The processes pertaining to each of the above blocks can be implemented with the controller 1400.

1. EEG Preprocessing and Epoch Extraction

Referring to FIG. 2, at a preprocessor block 210, the controller 1400 can process EEG signals for further analysis. For example, EEG signals from Fp1, Fp2, F7, and F8 electrodes may contain DC offset from Analog to Digital conversion and power line noise as interference. At the preprocessor block, controller 1400 may remove baseline noise by band pass filtering. The band pass filter may have a range of about 0.5 Hz to 30 Hz. For example, the band pass filter may have a frequency range of 0.5-25 Hz. The upper frequency range of 25 Hz can reduce the influence of muscle artifact during periods of light sedation and wakefulness. The controller 1400 may downsample the EEG signals. For example, the controller 1400 may downsample the EEG signals to 250 Hz.

At an EEG epoch segmentation block 212, the controller 1400 can segment the output from preprocessor block 210 into smaller epochs. For example, output from preprocessor block 210 may be one-minute EEG segments. The controller 1400 can segment the one minute EEG segments into 4-second epochs with 0.1 s shift. The output of the EEG epoch segmentation block 212 can be segmented EEG signals.

2. Feature Extraction

With continued reference to FIG. 2, at a feature extraction block 214, the controller 1400 can extract features in the EEG signals output from the EEG epoch segmentation block 212. The controller 1400 can use a set of some or all established features for the feature extraction. For example, the controller 1400 can use at least forty four QEEG features (from time, frequency and entropy domain). The QEEG features can be extracted from the segmented EEG signal(s). For example, the controller 1400 can extract 44 QEEG features from each 4 second epoch in each example bipolar montaged channel. Example features are shown in Table 1.

TABLE 1

| Domain | Features |
| --- | --- |
| Time | (1) Nonlinear energy operator, (2) Activity ($1^{st}$ Hjorth parameter), (3) Mobility ($2^{nd}$ Hjorth parameter), (4) Complexity ($3^{rd}$ Hjorth parameter), (5) Root mean square (RMS) amplitude, (6) Kurtosis, (7) Skewness, (8-11) mean, standard deviation, skewness and kurtosis of amplitude modulation (AM), (12) Burst suppression ratio/minute (BSR). |
| Frequency | (13) $PP_{\delta\delta}$ = mean power in delta band (0.5-4 Hz), (14) $PP_{\theta\theta}$ = mean power in theta band (4-8 Hz), (15) $PP_{\alpha\alpha}$ = mean power in alpha band (8-12 Hz), (16) $PP_{\sigma\sigma}$ = mean power in spindle band (12-16 Hz), (17) $PP_{\beta\beta}$ = power in beta band (16-25 Hz), (18) $PP_{TT}$ = total spectral power (0.5-25 Hz), (19-23) $PP_{\delta\delta}/PP_{TT}$, $PP_{\theta\theta}/PP_{TT}$, $PP_{\alpha\alpha}/PP_{TT}$, $PP_{\sigma\sigma}/PP_{TT}$, $PP_{\beta\beta}/PP_{TT}$, (24-27) $PP_{\delta\delta}/PP_{\theta\theta}$, $PP_{\alpha\alpha}/PP_{\theta\theta}$, $PP_{\sigma\sigma}/PP_{\theta\theta}$, $PP_{\beta\beta}/PP_{\theta\theta}$, (28-30) $PP_{\alpha\alpha}/PP_{\theta\theta}$, $PP_{\sigma\sigma}/PP_{\theta\theta}$, $PP_{\beta\beta}/PP_{\theta\theta}$, (31-34) mean, standard deviation, skewness and kurtosis of frequency modulation (FM) (35) spectral edge frequency, (36) peak frequency. |
| Entropy | (37) Singular value decomposition entropy, (38) spectral entropy, (39) state entropy, (40) sample entropy, (41) Renyi entropy, (42) Shannon entropy, (43) permutation entropy, (44) fractal dimension. |

At a median block 216, the controller 1400 can obtain a median across channels. The output of the median block 216 can include a set of features for the subject. For example, where the controller 1400 extracted 44 features across two channels for the subject at feature extraction block 214, the controller 1400 can determine a median of the features in the two channels, resulting in a dataset of 44 features for the subject. The controller 1400 can also use other averaging operators instead of taking median.

3. Classification and Post-Processing

With continued reference to FIG. 2, at a feature selection block 218, the controller 1400 can select features to train models to predict the probability of sedation level. For example, logistic regression with an elastic-net (EN) regularization method for feature selection can be used to train models to predict the probability of sedation level using the glmnet toolbox. For an elastic-net regularizaton method for feature selection, $Y \in \mathbb{R}^n$ can be the n×1 desired output, $X \in \mathbb{R}^{n \times p}$ can be a matrix of features or observations and $b \in \mathbb{R}^p$ a parameter vector. The elastic-net regularization estimation procedure can create a model that predicts Y as $\hat{Y}=b^TX$ by minimizing the square of the $l_2$-norm of the difference between the true response and the desired output response, and $l_1$, $l_2$ penalty factors which can be written as:

$$\operatorname*{argmin}_{b} \|Y - Xb\|_2^2 + \lambda((1-\alpha)\|b\|_2 + \alpha\|b\|_1)$$

where $\lambda$ is the penalty parameter, $\|\cdot\|_1$, $\|\cdot\|_2$ are the $l_1$-norm and $l_2$-norm, respectively, and $\alpha$ controls the relative contribution of the $\|\cdot\|_1$, $\|\cdot\|_2$ penalties. Setting $\alpha=1$ can result in least absolute shrinkage and selection operator (LASSO) and $\alpha=0$ can be equivalent to ridge regression. Elastic-net regularization feature selection method is ideal for datasets with multiple features that are highly correlated. In applicants where several highly correlated features are used, LASSO performs sparse selection, tending to select one feature and discarding the rest. Ridge regression can shrink the model coefficients towards each other for highly correlated features. The elastic-net produces sparse feature representation through $l_1$ penalty and selects corresponding features through $l_2$ penalty. In short, for a given $\lambda$ as $\alpha$ increases from 0 to 1, the number of sparse model coefficients (coefficients equal to 0) monotonically increase from 0 to LASSO sparse estimation. For example, $\alpha=0.5$ can be set for equal contribution from $\|\cdot\|_1$, $\|\cdot\|_2$ penalties.

At a DTC transform block 222, the controller 1400 can convert the predicted output $\hat{Y}=b^TX$ of the model to posterior probabilities via the logit transform to obtain the patient sedation level as:

$$P(Y=1 \mid X) = \frac{1}{1+\exp(-b^TX)}$$

This patient sedation level can indicate the sedation state of a patient. The patient sedation level can be a probability score on a continuous scale of 0 to 1. Thus, the output of the DTC transform block 222 can be a continuous score representative of patient sedation level.

4. Metrics

The area under the receiver operator characteristic curve (AUC) can be used to assess the performance of the logistic regression model. In addition, the Spearman rank correlation coefficient ($\rho$) can be obtained between the sedation level estimate and continuous MOAA/s assessments.

5. Cross Validation

Leave-one-out cross validation (LOOCV) can be used to assess performance of the prediction system, to provide an unbiased estimate of out-of-sample model performance. In one example, data from (N−1) subjects were used for parameter selection and model training and the left-out subject was used for testing. This process was repeated until the recording from each subject was used once for testing (N iterations in total). This LOOCV process can be referred to as outer cross validation to distinguish it from a separate inner cross validation process performed on each fold of the training data (see below). Whereas the purpose of outer cross validation may be to obtain an unbiased estimate of model performance, the purpose of inner cross validation may be optimization of model parameters.

6. Training

The training data can be selected for training based on a quality metric for the training data. For example, the training data may include MOAA/S scores. Since MOAA/S scores are subjective measures, scores closer to the extremes of 0 and 5 (e.g. scores 0, 1, and 4, 5) are more likely to be correct than scores in the center of the scale (e.g. scores 2, 3). Thus, to more accurately train the model, data relating to MOAA/S scores closer to the center of the MOAA/S scale may be excluded from the training data.

The training data (i.e. data from (N−1) subjects) can be used to select features for inclusion in the model and to estimate the optimal values for the coefficients in the linear regression model. Feature selection can involve selecting a hyperparameter λ in the elastic-net regularization function, such as 10-fold cross validation on the training data (i.e. dividing training data into 10 parts). In each fold of inner cross validation, a series of models can be trained using a range of penalty values λ, and tested each model on the remaining fold of the training data. The value of λ that minimizes the mean deviance across all 10 inner cross validation folds can be selected as the optimal λ and later used to train a single final model on all of the training data.

7. Testing

A model resulting from internal cross validation can be tested in the outer loop of LOOCV by evaluating its performance on the held-out testing data. The trained regression model with parameters that were optimal for the training data can be used to predict the probability of patient responses on the left-out testing data. Thus, the model selection routine can be performed only on the training data (using inner cross validation) and be independent from the testing data.

In some examples, nine different training and testing combinations were tested to demonstrate the effect of drug dependency (drug dependent system): 1) PP—train and test on propofol data, 2) SP—train on sevoflurane and test on propofol data, 3) DP—train on dexmedetomidine and test on propofol data, 4) SS—train and test on sevoflurane data, 5) PS—train on propofol and test on sevoflurane data, 6) DS—train on dexmedetomidine and test on sevoflurane data, 7) DD—train and test on dexmedetomidine data, 8) PD—train on propofol and test on dexmedetomidine data, and 9) SD—train on sevoflurane and test on dexmedetomidine data. In some examples, to test the performance of the system in drug independent mode (drug independent system), a cross-anesthetic model by pooling data from all three anesthetics was developed. For example, propofol, sevoflurane and dexmedetomidine data can be combined as one dataset and a LOOCV can be performed.

8. Statistical Analysis

In some examples, analysis of variance (ANOVA) followed by post-hoc testing with the Tukey Honest Significant difference test was used to assess group differences. In some examples, tests were two-sided with alpha=0.05. In some examples, coding and analysis was performed using the MATLAB 2018a scripting language (Natick, USA).

G. Example Application of Sedation Level Estimation System

1. Performance of Individual Features

Figure 3:
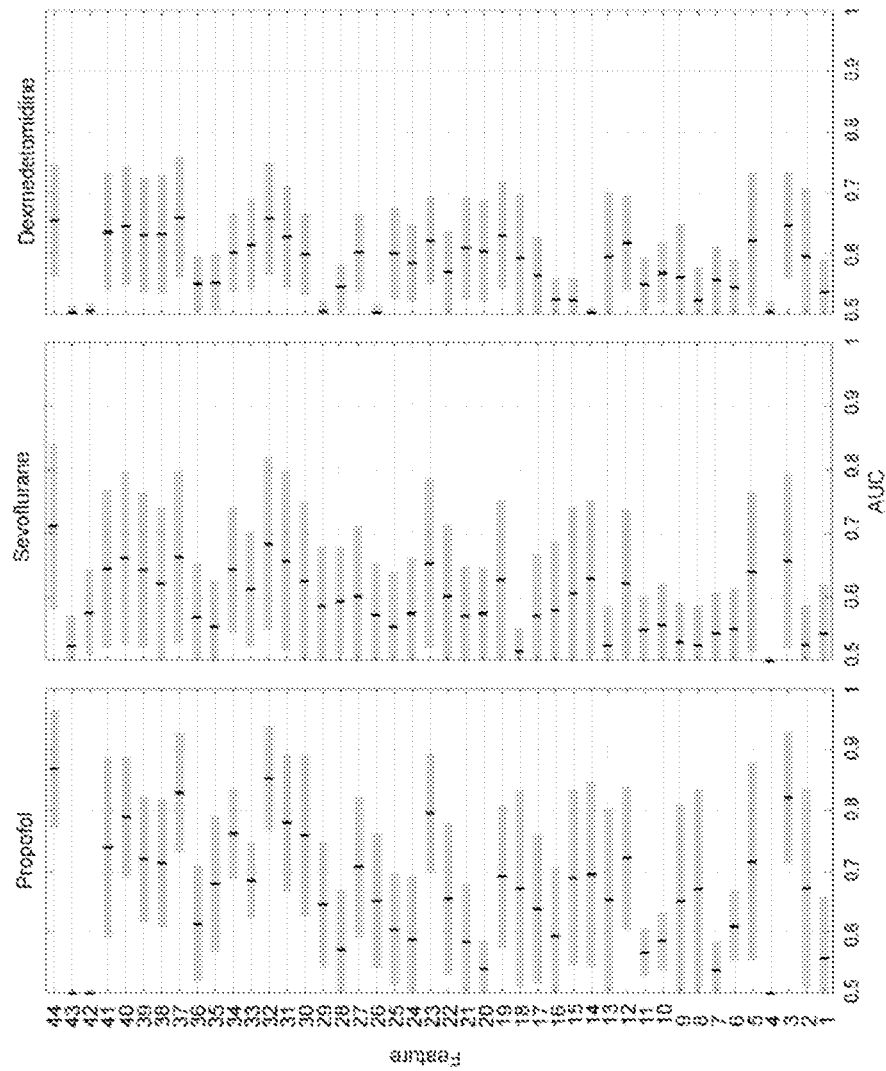
FIG. 3 illustrates an example distribution of AUC for individual features across a group of example drugs to discriminate between awake and sedated EEG epochs.

Example distributions of AUC values for individual features across three drugs are shown in FIG. 3. No single feature was able to efficiently differentiate between awake and sedated state for the three drugs illustrated in FIG. 3 (AUC>0.9). The relative entropy (RE) had the highest AUC for both propofol (AUC=0.87 (0.10)) and sevoflurane (AUC=0.71 (0.05)). For dexmedetomidine, singular value decomposition entropy outperformed other features (AUC=0.66 (0.05)).

2. Drug Dependent System

Figure 4:
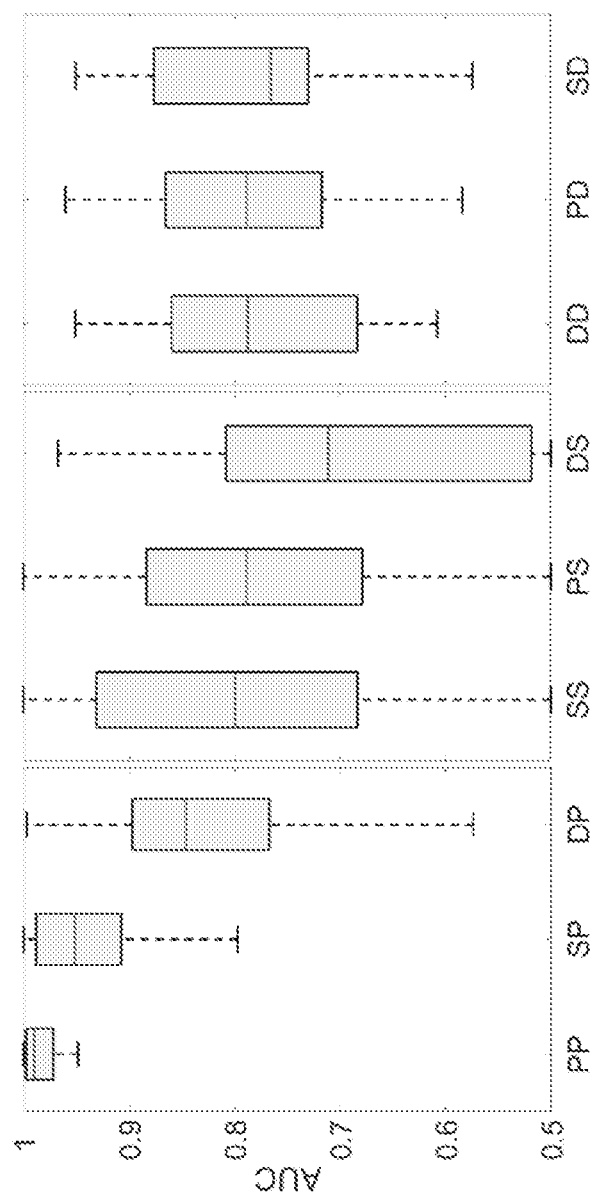
FIG. 4 illustrates boxplots showing an example distribution of the AUC of one example of the sedation level estimation system across nine training and testing combinations using an example combined set of features (QEEG features).

Example performance of the sedation level estimation system 200 using different feature domains is given in Table 2. As shown in Table 2, performance was significantly better (p<0.05) using combined QEEG features (time+frequency+entropy) when compared to other individual domain features. In some examples, the following performances were obtained for different training and testing combinations using QEEG features: PP—0.97 (0.03), SS—0.74 (0.25), DD—0.77 (0.10), SP—0.93 (0.06), DP=0.82 (0.11), PS=0.73 (0.23), DS=0.66 (0.18), PD=0.74 (0.09), and SD=0.71 (0.10). In some examples, the performance of the system when trained and tested on the same drug outperformed the system when trained and tested on different drugs. Example distributions of AUC values using QEEG features are shown in FIG. 4.

TABLE 2

| Feature | PP | SS | DD | SP | DP | PS | DS | PD | SD |
|---|---|---|---|---|---|---|---|---|---|
| Time | 0.9 | 0.67 | 0.75 | 0.87 | 0.87 | 0.67 | 0.66 | 0.73 | 0.74 |
|  | (0.08) | (0.23) | (0.09) | (0.10) | (0.10) | (0.21) | (0.22) | (0.10) | (0.09) |
| Frequency | 0.95 | 0.70 | 0.75 | 0.90 | 0.83 | 0.70 | 0.63 | 0.73 | 0.68 |
|  | (0.06) | (0.22) | (0.09) | (0.07) | (0.11) | (0.22) | (0.20) | (0.10) | (0.08) |
| Entropy | 0.96 | 0.72 | 0.77 | 0.95 | 0.91 | 0.71 | 0.67 | 0.80 | 0.79 |
|  | (0.04) | (0.23) | (0.10) | (0.05) | (0.07) | (0.24) | (0.24) | (0.09) | (0.10) |
| QEEG | 0.97 | 0.74 | 0.77 | 0.93 | 0.82 | 0.73 | 0.66 | 0.79 | 0.78 |
|  | (0.03) | (0.25) | (0.10) | (0.06) | (0.11) | (0.23) | (0.18) | (0.09) | (0.10) |

Table 2 shows example performance of an example of the sedation level estimation system 200 (AUC values across patients) using feature sets. Results are reported as mean (±standard deviation).

Abbreviations:

AUC, area under the curve;

PP, train and test on propofol;

SS, train and test on sevoflurane;

DD, train and test on dexmedetomidine;

SP, train on sevoflurane and test on propofol;

DP, train on dexmedetomidine and test on propofol;

PS, train on Propofol and test on sevoflurane;

DS, train on dexmedetomidine and test on sevoflurane;

PD, train on propofol and test on dexmedetomidine;

SD, train on sevoflurane and test on dexmedetomidine.

3. Drug Independent System

In one example of a drug independent system, data was combined from three anesthetic drugs (a total of 102 iterations), resulting in slight decrease in the performance of 2% for propofol (mean AUC=0.97 (0.03) to 0.95 (0.05), p=3.5E-4), 1% for sevoflurane (mean AUC=0.74 (0.25) to 0.73 (0.22), p=0.40), 1% in the case of dexmedetomidine (mean AUC 0.77 (0.10) to 0.76 (0.10), p=0.48), and an overall mean AUC=0.83 (0.17) using QEEG features.

Table 3 shows an example list of the top 20 features selected (reported as $$\frac{FT_N}{N} \times 100\%,$$

where $FT_N$=number of times a given feature was chosen across all subjects during training process, and N refers to number of patients in each drug class) by an EN algorithm across all subjects for propofol, sevoflurane and dexmedetomidine. Not all 44 QEEG features may be significant to the system and the features may vary across each patient.

TABLE 3

| Propofol | | Sevoflurane | | Dexmedetomidine | | Combined | |
|---|---|---|---|---|---|---|---|
| Feature | FTN | Feature | FTN | Feature | FTN | Feature | FTN |
| Kurtosis | 100 | Kurtosis | 100 | Kurtosis | 85.19 | Kurtosis | 37.89 |
| Skewness | 100 | std FM | 100 | Complexity | 85.19 | power in alpha band | 37.89 |
| power in delta band | 100 | fractal dimension | 100 | skewness AM | 85.19 | std FM | 37.89 |
| power in spindle band | 100 | power in alpha band | 96.88 | kurtosis AM | 85.19 | fractal dimension | 37.89 |
| spindle/total | 100 | Skewness | 84.38 | BSR | 85.19 | Skewness | 36.84 |
| alpha/delta | 100 | BSR | 84.38 | power in delta band | 85.19 | BSR | 36.84 |
| mean FM | 100 | theta/total | 84.38 | theta/total | 85.19 | power in spindle band | 36.84 |
| std FM | 100 | alpha/total | 84.38 | alpha/total | 85.19 | theta/total | 36.84 |
| kurtosis FM | 100 | alpha/delta | 84.38 | spindle/total | 85.19 | alpha/total | 36.84 |
| spectral edge frequency | 100 | alpha/theta | 84.38 | beta/total | 85.19 | alpha/delta | 36.84 |
| permutation entropy | 100 | beta/theta | 84.38 | spindle/theta | 85.19 | alpha/theta | 36.84 |
| fractal dimension | 100 | skewness FM | 84.38 | std FM skewness | 85.19 | beta/theta | 36.84 |
| Nonlinear energy operator | 97.22 | spectral edge frequency peak | 84.38 | FM spectral edge frequency | 85.19 | skewness FM | 36.84 |
| RMS amplitude | 97.22 | frequency Renyi entropy | 84.38 | Singular value decomposition entropy | 85.19 | kurtosis FM spectral edge frequency peak | 36.84 36.84 |
| power in beta band | 97.22 | Shannon entropy | 84.38 | state entropy | 85.19 | frequency | |
| state entropy | 97.22 | | | | | | |

Table 3 shows an example list of top 20 features and the number of times each feature was selected (reported as reported as $$\frac{FT_N}{N} \times 100\%,$$

where $FT_N$=number of times a given feature was chosen across all subjects during training process, and N refers to number of patients in each drug class) by EN algorithm across all subjects for propofol, sevoflurane and dexmedetomidine.

Figure 5:
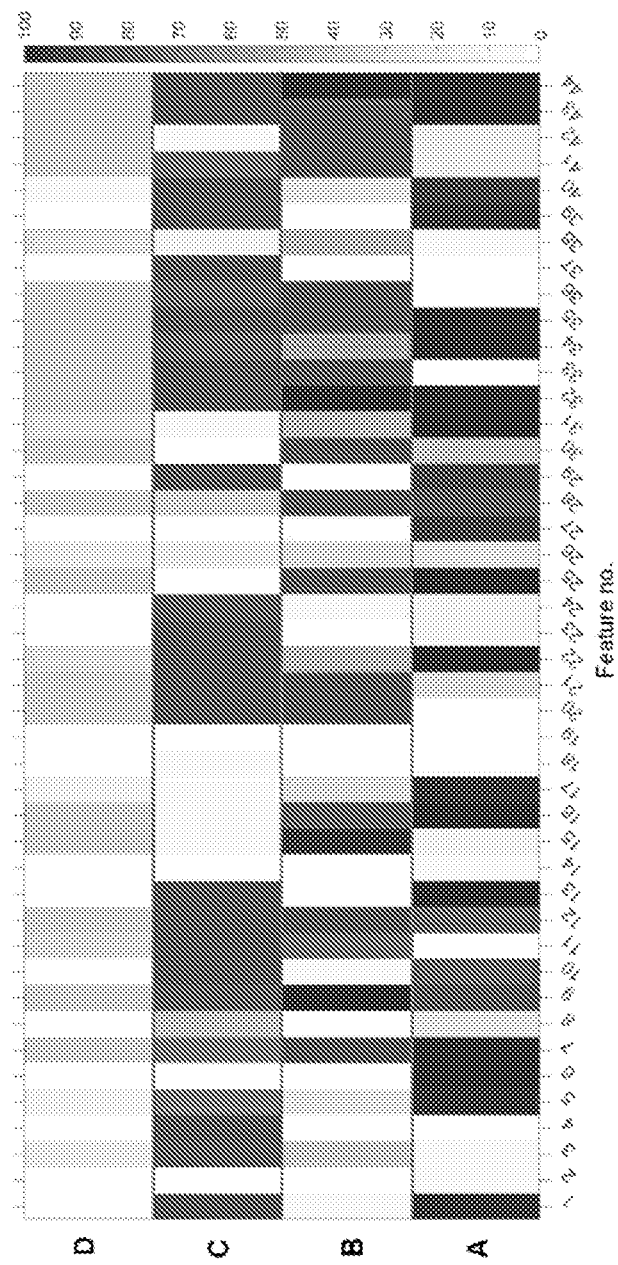
FIG. 5 illustrates an example heatmap illustrating the percentage number of times a given feature was selected by the elastic-net feature selection algorithm in drug independent mode for (A) propofol, (B) sevoflurane, (C) dexmedetomidine, and (D) combined drugs.

FIG. 5 shows an example heatmap of features selected by an example EN regularization feature selection method in drug independent mode for (A) propofol, (B) sevoflurane, (C) dexmedetomidine, and (D) combined drugs. The colorbar indicates the weightage assigned by an example elastic-net regularization algorithm to individual features for sedation level prediction. Higher intensity in the colormap indicates features that are more robustly informative (selected more consistently across different subjects during classifier training). Different combinations of features can be selected for each patient as part of the cross validation methodology in which different training data (all data except that subject's own data) are used for training the model to predict level of arousal on the testing subject. For example, features that were more consistently selected across all subjects for propofol, sevoflurane, and dexmedetomidine include Kurtosis, power in the alpha band, standard deviation of FM, and fractal dimension. Other common features selected are listed in Table 3. Certain features may correlate with greater levels of sedation. In some examples, a controller 1400 may select the features with greater correlations in order to determine a sedation level estimation. For example, the controller 1400 may select 3 features with the greatest correlation with sedation when selecting features from the testing data for analysis. The controller 1400 can store the selected features for use in new patients.

Figure 6:
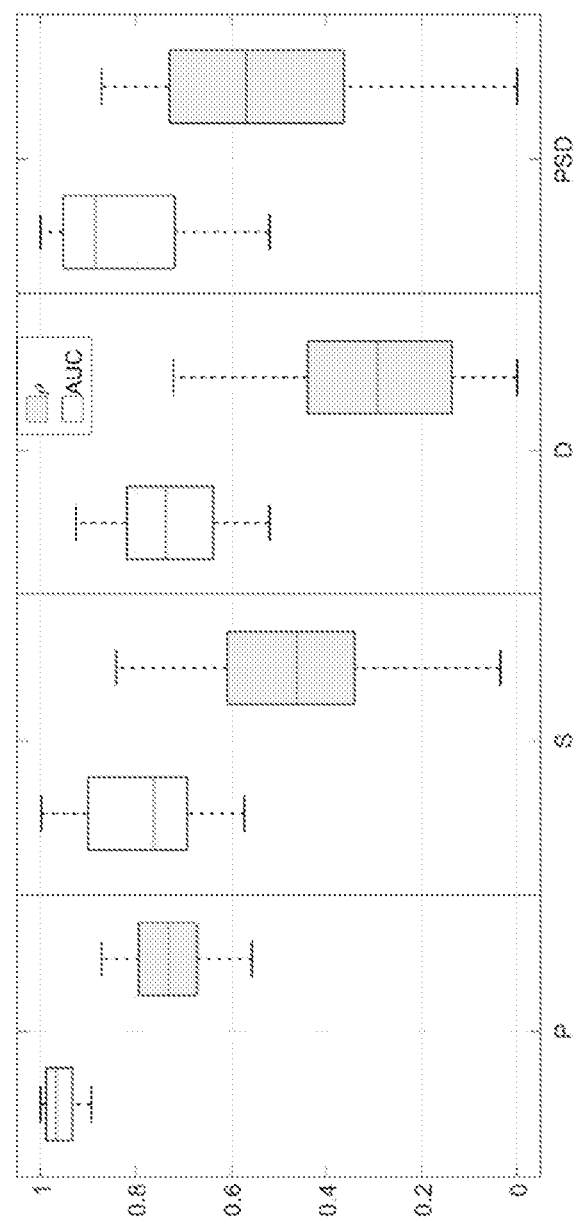
FIG. 6 illustrates example boxplots showing the distribution of performance metrics according to one example—(a) area under the curve (AUC) and (b) Spearman's correlation (p) of the sedation level estimation system 200 across different testing combinations in drug independent mode.

An example distribution of performance values of an example of the system in drug independent mode across different drugs is shown in FIG. 6. In particular, FIG. 6 illustrates boxplots showing the distribution of performance metrics according to one example—(a) area under the curve (AUC) and (b) Spearman's correlation (ρ) of the sedation level estimation system 200 across different testing combinations in drug independent mode. P may represent a model trained on combined data and tested on propofol data, S may represent a model trained on combined data and tested on sevoflurane data, D may represent a model trained on combined data and tested on dexmedetomidine data, and PSD may represent a model trained and tested on combined data.

H. Continuous Sedation Level Assessment

Using a multi-class classification or a multinomial regression may not be efficient due to the annotation noise and limited dataset in intermediate sedation states which will provide a discrete score. To overcome these limitations, a model may be trained by the controller 1400 to discriminate between two extreme levels of sedation and use a logit transform to convert it into a continuous probability sedation level score or patient state index. This approach is beneficial because MOAA/S scores are not continuous response assessments, (i.e. they are performed intermittently), and can therefore limit the number of assessments in individual scores, creating an imbalanced dataset. Additionally, the approach is beneficial because it can reduce the score "annotation-noise" due to interobserver variability during sedation level assessment.

A continuous sedation level or patient state index can be obtained by developing a binary classifier, which is trained only on awake and sedated epochs, to assign a probability score to all EEG epochs corresponding to all MOAA/S scores (0 to 5). For example, the controller 1400, through a binary classifier, may determine a probability score of 0.6 or 60% probability of the patient being sedated for an epoch having a MOAA/S score of 3. The Spearman rank-correlation (p) can then be obtained between a binary classifier sedation level and all MOAA/S scores. For example, the controller 1400 may determine a probability score for a number of epochs that may have a range of MOAA/S scores. The controller 1400 may then determine a correlation between that dataset and the MOAA/S scores. That correlation can be used to generate a continuous sedation level estimation. Once determined, the correlation can be used to generate a continuous sedation level estimate as part of a patient monitoring system.

Table 4 summarizes the performance of the system 200 to predict a continuous sedation level. In one example, this approach provided promising results, with a mean p=0.54 (0.21) significantly better than a random chance p=0.12 (0.09), suggesting that the system trained as a binary model may ultimately provide a continuous level estimation of sedation level.

Figure 7:
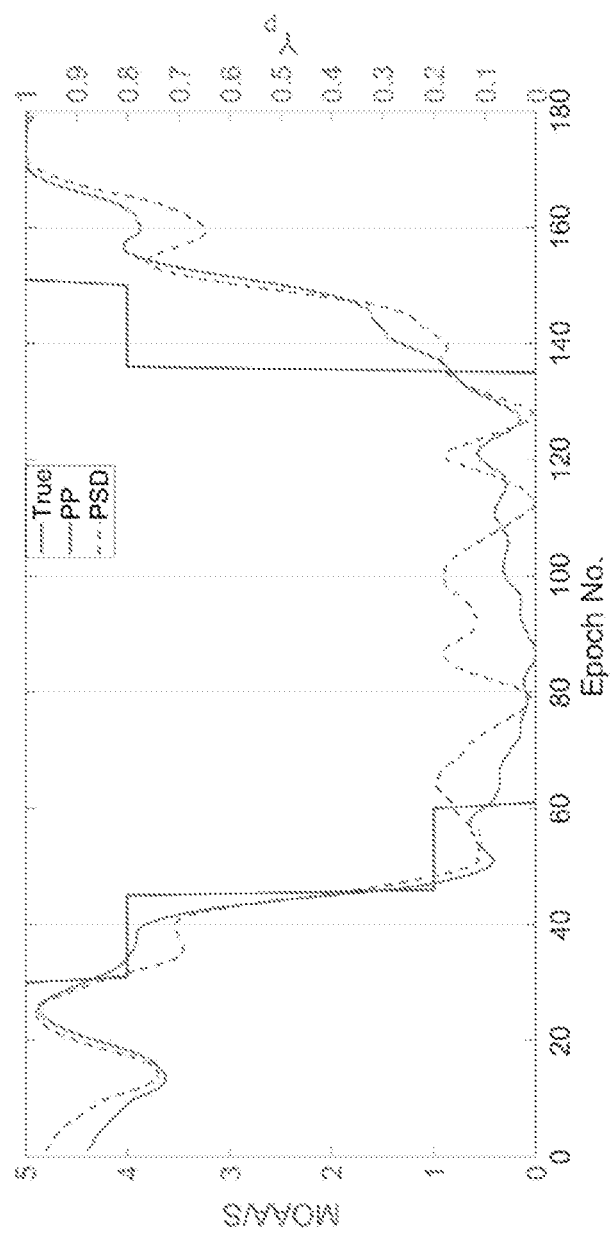
FIG. 7 shows an example illustration of the correlation between the output of an example sedation level estimation system 200 and example Modified Observer's Assessment of Alertness/Sedation Scale (MOAA/S) assessments.

FIG. 7 shows an example illustration of the correlation between the output of an example sedation level estimation system 200 and example Modified Observer's Assessment of Alertness/Sedation Scale (MOASS) assessments. In the example shown in FIG. 7, a trained binary logistic regression model (trained only on awake and sedated epochs) is used to obtain continuous probability score (Yp) on the testing volunteer. "True" may correspond to MOAA/S scores, PP may correspond to a model trained and tested on propofol data (p=0.71), and PSD may correspond to a model trained on combined data and tested on propofol data (p=0.65).

TABLE 4

| Drug | Time | | Frequency | | Entropy | | QEEG | |
|---|---|---|---|---|---|---|---|---|
| | AUC | ρ | AUC | ρ | AUC | ρ | AUC | ρ |
| Propofol | 0.88 | 0.58 | 0.92 | 0.67 | 0.93 | 0.70 | 0.94 | 0.72 |
| | (0.08) | (0.17) | (0.05) | (0.10) | (0.04) | (0.09) | (0.05) | (0.09) |
| Sevoflurane | 0.65 | 0.39 | 0.67 | 0.40 | 0.69 | 0.44 | 0.73 | 0.48 |
| | (0.22) | (0.20) | (0.21) | (0.19) | (0.23) | (0.20) | (0.22) | (0.19) |
| Dexmedeto-midine | 0.73 | 0.33 | 0.74 | 0.33 | 0.72 | 0.31 | 0.76 | 0.35 |
| | (0.09) | (0.15) | (0.10) | (0.16) | (0.10) | (0.15) | (0.10) | (0.17) |
| Combined drugs | 0.77 | 0.45 | 0.78 | 0.49 | 0.80 | 0.51 | 0.82 | 0.54 |
| | (0.18) | (0.20) | (0.18) | (0.21) | (0.18) | (0.21) | (0.17) | (0.21) |

Table 4 shows example performance of an example of the patient sedation level estimation system 200 (mean AUC values across patients) in drug independent mode using feature sets. Results are reported as mean, ±standard deviation.
Abbreviations:
AUC, area under the curve;
ρ, Spearman's rank correlation.

I. Nonlinear Machine Learning Models

In addition to the models discussed above, the controller 1400 can also use alone or in combination non-linear machine learning models. In total, 204 EEG recordings from 66 healthy volunteers were used to determine performance of several nonlinear machine learning algorithms to predict sedation levels or patient state index. In some instances, the following disclosure can be used to develop a robust and reliable real-time automatic sedation level prediction system implemented by the controller 1400 that is invariant across all conditions.

Each volunteer was scheduled to receive four sessions of anesthesia with different drug combinations in a random order, with a minimal interval of one week between sessions. The four sessions were named "propofol alone", "sevoflurane alone", "propofol combined with remifentanil", and "sevoflurane combined with remifentanil". In each session that needed blood sampling, the volunteer received an arterial line before any drug was administered. Propofol and remifentanil were administered through an intravenous line by a Fresenius Base Primea docking station (Fresenius-Kabi, Bad Homburg, Germany) carrying two Fresenius Module DPS pumps, that were controlled by RUGLOOPII software (Demed, Temse, Belgium) in order to steer target-controlled infusion (TCI). RUGLOOPII is a computer-controlled drug delivery and data collection software package. Both drugs were titrated towards a target effect-site concentration using a three compartmental pharmacokinetic-dynamic (PKPD) model enlarged with an effect-site compartment. For propofol, the pharmacokinetic-dynamic (PKPD) model of Schnider et al 2 was used to predict the effect-site concentration (CePROP). For Remifentanil, the effect-site concentration (CeREMI) was predicted by the PKPD model of Minto et al. 3. Sevoflurane was titrated using the proprietary closed loop algorithm of the Zeus® ventilator (Software version 4.03.35, Dräger Medical, Lübeck, Germany) to target and maintain a constant end-tidal sevoflurane (ETSEVO).

Each session contained two separate titration-phases: a stepwise up and down administration of drugs towards consecutive steady state conditions. The sequence of events and study observations are shown in the original study 1. After 2 minutes of baseline measurements, a "staircase" step-up and step-down infusion of anesthetic drugs was administered. For the propofol alone group, the initial CePROP was set to 0.5 μg mL−1 followed by successive steps toward target concentration of 1, 1.5, 2.5, 3.5, 4.5, 6 and 7.5 μg mL−1. For the sevoflurane alone group, the initial ETSEVO was set to 0.2 vol % followed by successive ETSEVO of 0.5, 1, 1.5, 2.5, 3.5, 4, 4.5 vol %. The upwards staircase was followed until tolerance/no motoric response to all stimuli was observed and a significant burst suppression ratio of at least 40% was attained. Next, the downward staircase steps were initiated, using identical targets but in reverse order. For the sessions with remifentanil, the same procedure was conducted, although 2 minutes prior to the start of propofol or sevoflurane, a CeREMI of 2 or 4 ng mL−1 was targeted in accordance with the stratification and maintained during the entire study. After the predicted CePROP or ETSEVO reached the target at each step, an equilibration time of 12 minutes was maintained to allow optimal equilibration between plasma- or end-tidal concentration and the corresponding effect-site concentration resulting in a pharmacological condition called a "pseudo-steady state."

After the 12 minutes of equilibration time, an additional minute of baseline electroencephalographic and hemodynamic measurements was performed. Thereafter, the Modified Observer's Assessment of Alertness/Sedation (MOAA/S) scale 4 was scored followed by two minutes of response time. This score is ranging from 5 (responding readily to name spoken in normal tone) to 0 (not responding to a painful trapezius squeeze). The observed MOAA/S is followed by drawing an arterial blood sample for analyzing the concentration of propofol and/or remifentanil. For sevoflurane, the measured ETSEVO at this steady-state condition was registered. A schematic diagram of the order of events can be found in the supplements of the original study1. Two minutes after MOAA/S, an electrical stimulus was administered during maximal 30 seconds and the tolerance/motoric responsiveness to electrical stimulation was observed, again followed by two minutes of response time.

In each session, the volunteers started by breathing spontaneously through a tight-fitting face mask connected to an anesthesia ventilator (Zeus®, Software version 4.03.35, Dräger Medical, Lübeck, Germany). End-tidal sevoflurane (ETSEVO), carbon dioxide and oxygen concentration were measured using a gas-analyzer of the anesthesia ventilator. If deemed necessary, respiratory support was applied to guarantee an unobstructed airway, adequate oxygenation ($SpO2>92\%$) and $CO2$ (35-45 mmHg) homeostasis. Throughout the study, all volunteers were connected to a vital signs monitor to monitor the oxygen saturation (measured by pulse oximetry), electrocardiogram (ECG) and intermittently measured non-invasive blood pressure at 1-min intervals.

Raw electro-encephalographic waves were measured using a 16 channel Neuroscan® EEG monitor (Compumedics USA, Limited, Charlotte, NC, USA) existing of a SynAMPRT headbox (model 9032) and system unit, that respectively collected and amplified the raw electro-encephalographic signals towards a laptop computer running SCAN4 proprietary recording software (Compumedics, Charlotte, USA). The volunteer wore a cap over the head mounted with standard 10-20 electrode montage. Through these electrodes we recorded raw EEG of locations A1, A2 (references on left and right earlobe), F3, Fz, F4 (electrodes in the cap above the motor cortex and frontal lobes), T7, C3, Cz, C4 and T8 (electrodes above the temporal parietal lobes and the somatosensory cortex), P3, Pz, P4 (electrodes above the occipital region) and Oz as a cranial and centrally located reference point). In addition, a bilateral PSI electrode was attached on the forehead of the volunteer and connected to a Masimo Root Monitor (Model-RDS-7, Masimo, Irvine, USA) that runs SEDLine® brain function software, in concordance with the manufacturer's instructions (Masimo Inc., Irvine, USA). This frontal adhesive electrode recorded 4 additional channels being: L1, R1, L2, R2 (L1 and R1 are the Fp1 and Fp2 leads of the standard 10-20 system). Even and uneven numbers in the standard 10-20 electrode montage correspond respectively to the right and left side of the brain.

Figure 12:
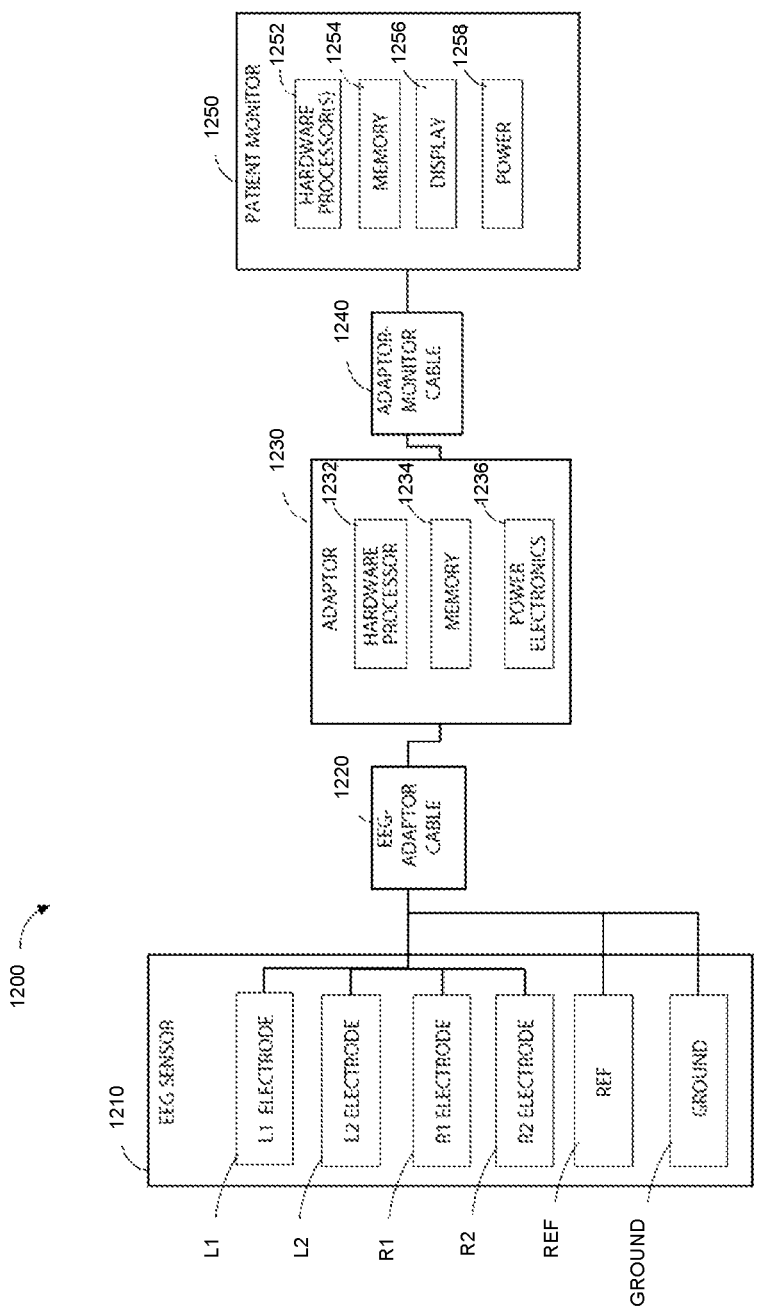
FIG. 12 illustrates a block diagram of an EEG hardware system.
Figure 13:
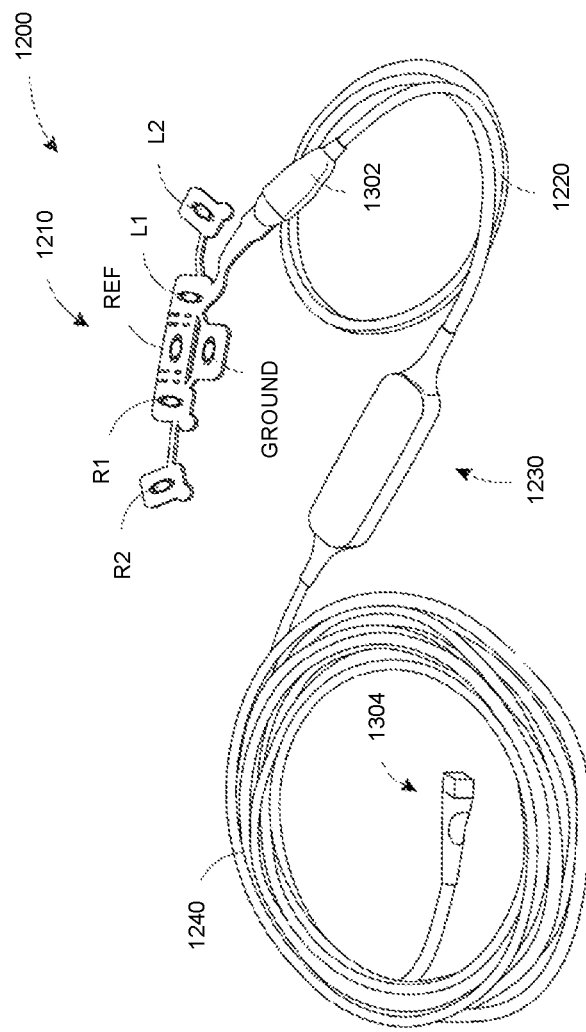
FIG. 13 illustrates an embodiment of the EEG hardware system shown in FIG. 12.

An example Masimo SEDLine connection cable used here is described with respect to FIGS. 12 and 13. For each lead of raw signal, a splitter was connected in order to allow simultaneous recording of the raw electroencephalogram by both SCAN4 (for storing high resolution raw EEG signals) and Masimo SEDLine software (for calculating electroencephalographic derived patient state index). The impedance of all electrodes was checked using the SCAN4 impedance algorithm. Impedance is indicated with a color code for every lead and screenshots of the impedance test-results were stored both before and after the drug administration. When impedance was higher than 30.7 kOhms, it was optimized by applying local pressure on the electrode (using adhesive tape) and/or adding additional lubricating gel.

Propofol (2,6-diisopropylphenol) plasma concentrations were measured using a validated gas chromatography-mass spectrometric analysis, whereas remifentanil plasma concentrations were measured using a liquid chromatography-tandem mass 5.

Patient Inclusion

Subjects were Included Age- and Sex Stratified into 3 Age Categories (18-34, 35-49 and 50-70 years). Volunteers were excluded if their body mass index was greater than 30 kg/m2 or less than 18 kg/m2, if they had any significant cardiovascular risk factor or disease, if they had neurological disorders, suffered from dementia, schizophrenia, psychosis, drug or alcohol abuse or daily use of more than 20 g of alcohol, depression requiring anti-depressive drug treatment or when they recently used psycho-active medication. Furthermore, volunteers could not participate in this trial when they were pregnant or breastfeeding, had a bilateral non-patent arteria ulnaris or suffered from any relevant medical condition.

Study Design

Each volunteer underwent two study sessions with at least one week between both sessions. On the first study day, volunteers received dexmedetomidine administered through target-controlled infusion (TCI) with targeted effect site concentrations of consecutively 1, 2, 3, 5 and 8 ng/ml. On their second study day (>1 week later), subjects received a similar stepwise increasing infusion of remifentanil with effect site targets of 1, 2, 3, 5 and 7 ng/ml. Consecutively, after allowing remifentanil to washout, volunteers received dexmedetomidine TCI with a targeted effect site concentration of 2 ng/ml. As soon as this effect site concentration was reached, an infusion of remifentanil was added with increasing effect site target concentrations of respectively 0.5, 1.0, 1.5, 2.0, 2.5, 3.0 and 4.0 ng/ml.

Study Procedures

Study participants were instructed to fast from 6 h before the start of their scheduled study sessions. Furthermore, they were instructed not to consume alcohol for 2 days prior to the study, not to smoke tobacco for 1 week and not to use recreational drugs for 2 weeks prior to their study days. When they arrived at the research unit, a 20-gauge intravenous cannula was placed and subjects were connected to a vital signs monitor. Under ultrasound guidance and after injection of a local anesthetic, a 20-gauge arterial cannula was placed for blood sampling and hemodynamic monitoring. During the study sessions a nurse anesthetist and anesthesiologist were present and responsible for the drug administration, monitoring, respiratory support and providing emergency care when needed. A complete anesthetic workstation was present as well as an anesthesia ventilator (Zeus Infinity C500 ventilator, Dräger Medical, Lübeck, Germany). A research physician and nurse performed all other study procedures. Volunteers were connected to the ventilator using a tight-fitting face mask with an inspired oxygen fraction set to 25%. The anesthesiologist supported respiration, if deemed necessary, by verbal stimulation, jaw thrust or chin lift, or by adding pressure support or positive pressure ventilation using the anesthesia ventilator.

Assessment of Cerebral Drug Effect

The cerebral drug effect was measured using 17-channel electroencephalography (EEG), with a BrainAmp DC32 amplifier and a Brainvision recorder (Brain Products GmbH, Gilching, Germany) recording at a sampling rate of 5 kHz. Furthermore, the level of sedation was tested at baseline, at each infusion step and during the recovery phase, using the MOAA/S score. In addition, prior to each increase in infusion step, a laryngoscopy was performed if the MOAA/S score was less than 2. Before the start of the infusions, volunteers were placed in supine position and they were asked to close their eyes. Except for the MOAA/S assessments, volunteers were not stimulated and ambient noise was kept low throughout the study session. Prior to the start of the drug infusions, baseline measurements of EEG and vital sign parameters were performed during a 5-minute period.

Drug Administration

Dexmedetomidine and remifentanil were both administered using target-controlled infusion. For dexmedetomidine, this TCI was based on the pharmacokinetic and pharmacodynamic (PKPD) models developed by Hannivoort and Colin et al. 6 using the effect site of the MOAA/s. For the first 3 infusion targets, the infusion rate was limited to 6 μg·kg−1·h−1 and for the highest two targets to 10 μg·kg−1·h−1. This was done in order to decrease initial hypertensive reactions as seen with bolus administration. To target remifentanil effect site concentrations, a PKPD model developed by Eleveld et al 7 was used.

Recovery Phase

Drug infusion was stopped after completion of all infusion steps or after a subject tolerated a laryngoscopy. In addition, when one of the safety criteria was met and deemed relevant by the anesthesiologist, drug infusion was also ceased.

Those safety criteria were:
- An change >30% in mean arterial blood pressure compared to baseline for more than 5 minutes
- A heart rate<40 bpm lasting more than 5 minutes
- A change in cardiac rhythm or conduction
- Any other safety reason (decided by the attending anesthesiologist)

Rescue medication with 0.5 mg atropine was administered if deemed necessary and then dexmedetomidine and/or remifentanil infusion was ceased. For maintaining acceptable blood pressure, volunteers were put in a slight Trendelenburg position. A rescue dose of 5 mg ephedrine was administered if needed and then drug infusion was ceased.

After cessation of drug infusion, the recovery phase began. Measurements and monitoring continued until the volunteer met the criteria of our hospitals post anesthesia care unit, then after also the last blood sample was taken, he or she was discharged home.

Blood Sampling, Storage and Analysis

Blood samples were drawn from the arterial line at baseline prior to changing the targeted effect site concentration (at steady-state), and at predefined time points during the recovery period. The samples were collected in EDTA tube and stored on ice for a maximum of 15 minutes for remifentanil or 1 hour for dexmedetomidine. Samples were centrifuged at 4° C. for 5 minutes and with 1,754×g (Labofuge 400R, Heraeus Holding GmBh, Hanau, Germany). The plasma was then transferred into cryovials. Sample stability for remifentanil was improved by adding 1.5 μL of formic acid per milliliter of plasma. The cryovials were then stored at or below −20° C.

Analysis of plasma concentrations was done using ultra-high-performance liquid chromatography-mass spectrometry (UPLC-MS/MS by a Xevo Triple Quadrupole mass spectrometer, Waters Corporation, Milford, Massachusetts, USA). The upper and lower limits of quantification were 20 ng/ml and 0.05 ng/ml respectively for both drugs. Samples thought to be above the upper quantification limit were diluted prior to sample treatment. The coefficient of variation was below 9% for remifentanil and below 8% for dexmedetomidine.

As discussed above, the Modified Observer's Assessment of Alertness/Sedation (MOAA/S) score 15 was used to assess the level of sedation. A MOAA/S score of 5 indicates awakeness and MOAA/S=0 corresponds to a deep sedated state. A binary classification between two MOAA/S subgroups: awake [MOAA/S 5 and 4] versus sedated [MOAA/S 1 and 0], discarding the remaining MOAA/S scores was performed.

Sedation Level Prediction System

Figures 8A, 8B:
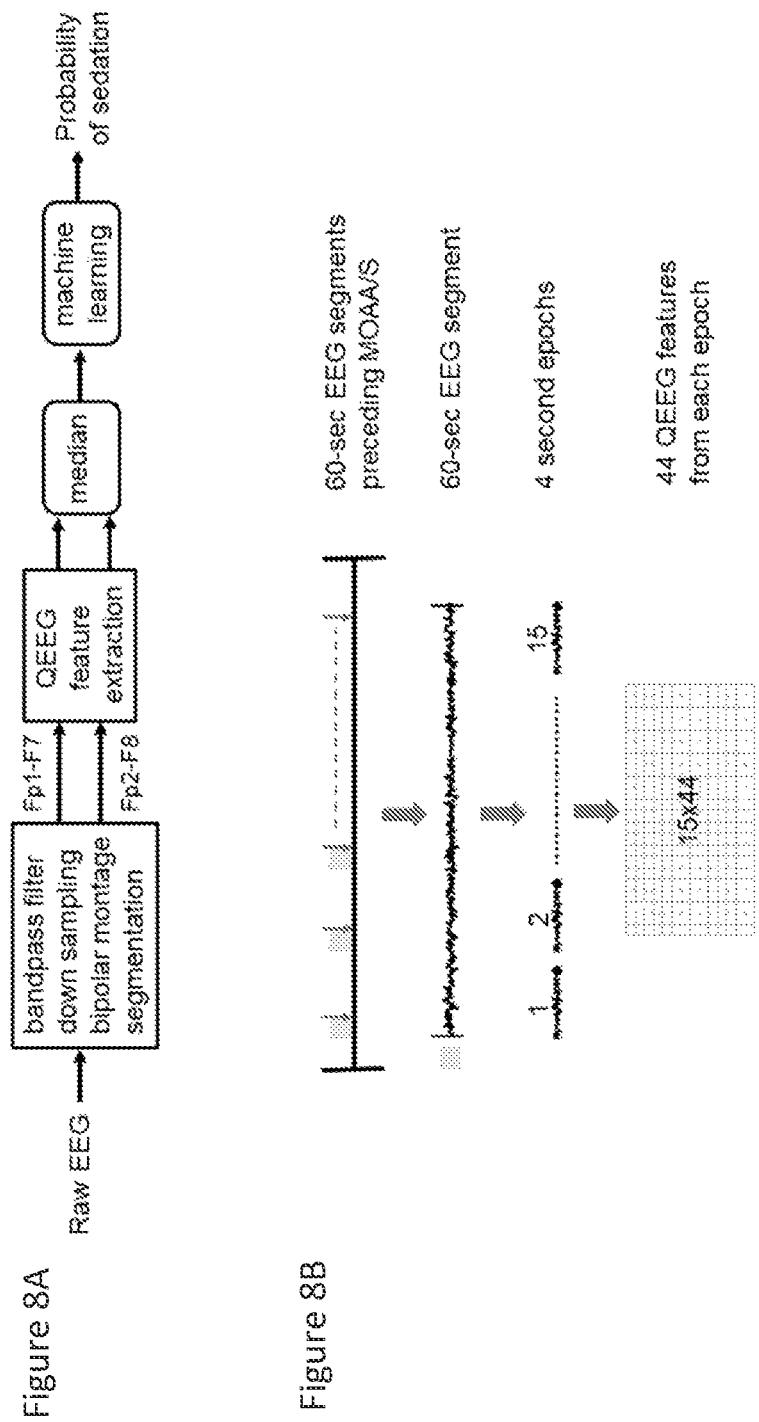
FIG. 8A shows the architecture of an example sedation level prediction system.
FIG. 8B shows signal processing of each one minute EEG segment that was further divided into 4 seconds small duration epochs for analysis.

FIG. 8A shows the architecture of the example sedation level prediction system that can be implemented with the controller 1400 and the EEG hardware systems described below. EEG was recorded using 17 channels according to international 10-20 system described in the supplementary material 1. For practical reasons, only used four frontal EEG channels, re-referenced in bipolar montage: Fp1—F7 and Fp2—F8 for developing the prediction model. The controller 1400 can be used to bandpass filtered the signal (using a zero-phase second order Butterworth bandpass filter) between 0.5-25 Hz and resampled to 250 Hz. From the downsampled signals, the controller 1400 can extract one minute EEG segments preceding the MOAA/S assessments with an assumption that they correspond to the assessed MOAA/S score. Each one minute EEG segment was further divided into 4 seconds small duration epochs for further analysis (see FIG. 8B).

The controller 1400 can extract the following 44 quantitative EEG (QEEG) features from each 4 s EEG epoch in this study:

Time domain—(1) Nonlinear energy operator, (2) Activity ($1^{st}$ Hjorth parameter), (3) Mobility ($2^{nd}$ Hjorth parameter), (4) Complexity ($3^{rd}$ Hjorth parameter), (5) Root mean square (RMS) amplitude, (6) Kurtosis, (7) Skewness, (8-11) mean, standard deviation, skewness and kurtosis of amplitude modulation (AM), (12) Burst suppression ratio/minute (BSR);

Frequency domain—(13) $P_\delta$=mean power in delta band (0.5-4 Hz), (14) $P_\theta$=mean power in theta band (4-8 Hz), (15) $P_\alpha$=mean power in alpha band (8-12 Hz), (16) $P_\sigma$=mean power in spindle band (12-16 Hz), (17) $P_\beta$=power in beta band (16-25 Hz), (18) $P_T$=total spectral power (0.5-25 Hz), (19-23) $P_\delta/P_T$, $P_\theta/P_T$, $P_\alpha/P_T$, $P_\sigma/P_T$, $P_\beta/P_T$, (24-27) $P_\delta/P_\theta$, $P_\alpha/P_\theta$, $P_\sigma/P_\theta$, $P_\beta/P_\theta$, (28-30) $P_\alpha/P_\theta$, $P_\sigma/P_\theta$, $P_\beta/P_\theta$, (31-34) mean, standard deviation, skewness and kurtosis of frequency modulation (FM) (35) spectral edge frequency, (36) peak frequency;

Entropy domain—(37) Singular value decomposition entropy, (38) spectral entropy, (39) state entropy, (40) sample entropy, (41) Renyi entropy, (42) Shannon entropy, (43) permutation entropy, (44) fractal dimension.

These features can be extracted separately for each bipolar frontal montage channel and then obtained a median across channels to combine the channel information. These features were then used to train a machine learning algorithm to obtain the probability of the sedated state for each 4 s EEG epoch.

Metrics

The controller 1400 can use the area under the receiver operator characteristic curve (AUC) to evaluate the model performance. The controller 1400 can also report sensitivity, specificity, F1-score for the best performing machine learning model.

Machine Learning Model Development

The controller 1400 can evaluate the performance of four machine learning algorithms: elastic net logistic regression (EN-LR), support vector machine with Gaussian kernel (SVM-G), random forest (RF), and Ensemble tree with bagging (ET-B). The controller 1400 can evaluate the performance of the proposed system using a leave-one-out cross-validation technique i.e. the controller 1400 divided the data into N−1 folds. In each iteration, the controller 1400 used N−1 EEG recordings for training the machine learning model and the left-out unseen recording for testing, resulting in a total of N iterations. In each fold, features in the training data were Z-score standardized (by subtracting the mean and dividing by the standard deviation) and the testing data features were normalized with respect to the Z-score normalization factor of the training data before using them for classification. The controller 1400 performed grid search to identify the optimal hyper-parameters of these models (summarized in supplementary table 1) through 10-fold cross-validation within the training data and the final optimal model was then used to estimate the sedation level probability on the testing data. This was repeated until each data was used once for testing and is illustrated in FIG. 8.

SUPPLEMENTARY TABLE 1

Summary of the grid search range used to tune machine learning hyperparameters. The optimal value refers to the value obtained during the training process.

| Model | Hyperparameter | Grid search range (min, max, step size) | Optimal parameter |
|---|---|---|---|
| EN-LR | α (Regularization) | 0, 1, 0.1 | 0.9 |
| SVM-G | γ = gaussian kernel, C = cost function | 0.1, 100, 0.1 | γ = 2.5, C = 50 |
| RF | number of trees | 50, 1000, 10 | 500 |
| ET-B | Number of learning cycles | 10, 200, 5 | 30 |

First, the controller 1400 performed binary classification to differentiate between awake and sedated state using pooled dataset during propofol, sevoflurane and dexmedetomidine infusion. Then the controller 1400 added remifentanil data to this pooled dataset to evaluated the robustness and stability of the machine learning models. By this way the controller 1400 identified the machine learning model that is invariant after the addition of new drug (remifentanil in this case).

Performance of Individual QEEG Features

Figure 9:
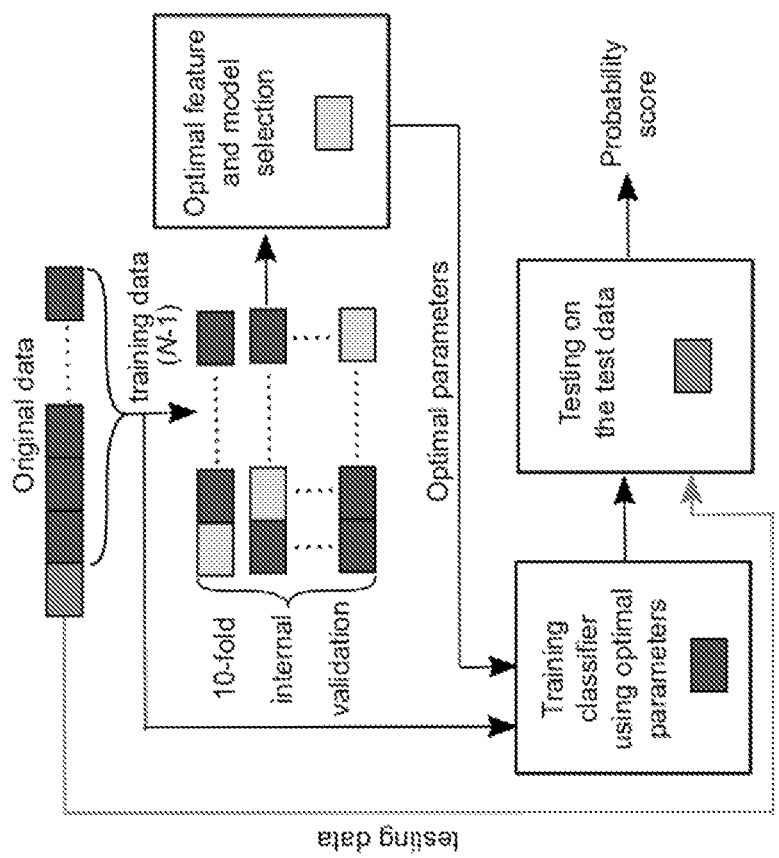
FIG. 9 shows the performance of individual features to discriminate between awake and sedated states with and without remifentanil.

FIG. 9 shows the performance of individual features to discriminate between awake and sedated states with and without remifentanil. Interaction with remifentanil significantly dropped the performance of all features. Fractal dimension provided the highest AUC of 0.74 (0.71-0.75) without remifentanil and dropped to 0.66 (0.64-0.68) after the addition of remifentanil.

Performance of Machine Learning Models

The performance of different machine learning models to predict sedation levels using the proposed architecture is summarized in table 1, shown below. The performance of ensemble tree with bagging outperformed other machine learning models and was stable after the inclusion of remifentanil

| | AUC | | |
|---|---|---|---|
| Model | without remifentanil | with remifentanil | P-value |
| EN-LR | 0.89 (0.81-0.92) | 0.85 (0.80-0.88) | 0.02 |
| SVM-G | 0.85 (0.77-0.88) | 0.84 (0.75-0.89) | 0.04 |
| RF | 0.83 (0.76-0.87) | 0.82 (0.75-0.88) | 0.06 |
| ET-B | 0.88 (0.85-0.91) | 0.87 (0.84-0.89) | 0.06 |

All models had AUC's above 0.8 without remifentanil but the AUC's dropped significantly when interacted with remifentanil. However, the performances of the tree based methods were not sensitive to the addition of remifentanil and the ET-B model achieved the highest AUC of 0.88 (0.84-0.89). All subsequent results will be based on the performance of ET-B including remifentanil.

Discriminative Features

Figure 10:
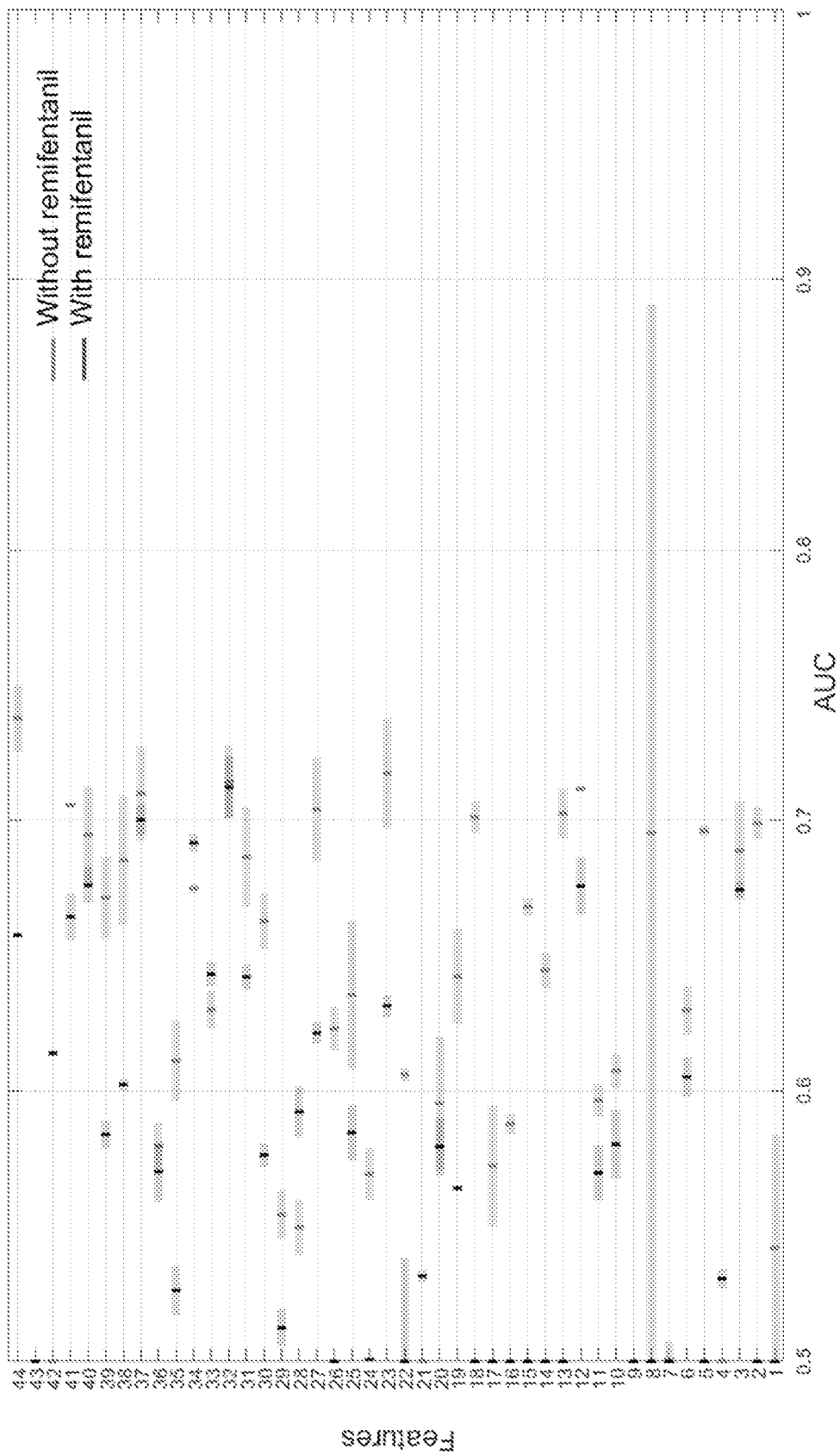
FIG. 10 illustrates the heatmap of weights assigned by the ET-B algorithm to individual features across all iterations.

FIG. 10 illustrates the heatmap of weights assigned by the ET-B algorithm to individual features across all iterations. Different features were selected in different iterations and 6 features were highly discriminatory (normalized weight≥0.3) without remifentanil: BSR, $P_\beta$, $P_\beta/P_T$, standard deviation of FM, SVDE, and FD. After the inclusion of remifentanil 12 features had weights above 0.3: NE, mobility, complexity, BSR, $P_\alpha$, $P_o$, $P_\alpha/P_\theta$, standard deviation of FM, kurtosis of FM, SVDE, SE, and FD.

Effect of Age

To evaluate the effect of age on the performance of the ET-B model, the controller 1400 divided the dataset into three sub groups: group1 —18 to 35 years, group 2 —35 to 50 years and group 3 —50 to 70 years. The controller 1400 then performed three different training testing combinations: (i) train on group 1 test on groups 2 and 3, (ii) train on group 2 test on groups 1 and 3 and (iii) train on group 3 test on groups 1 and 2. The following table provides summary of AUC's (mean AUC (95% CI)) obtained for each model when trained and tested across different age groups.

| | Group 1 | Group 2 | Group 3 |
|---|---|---|---|
| Group 1 | 0.89 (0.79-0.95) | 0.75 (0.74-0.76) | 0.73 (0.71-0.74) |
| Group 2 | 0.77 (0.75-0.79) | 0.88 (0.77-0.95) | 0.80 (0.78-0.82) |
| Group 3 | 0.78 (0.77-0.79) | 0.83 (0.81-0.84) | 0.89 (0.76-0.95) |

The performance of the model was nearly similar when trained and tested within the same age group, however, it dropped significantly (approximately 10% reduction in the overall AUC) during cross training and testing (trained and tested on different groups).

Effect of Sex

To evaluate the influence of sex, the controller 1400 performed cross training and testing i.e, the controller 1400 trained the ET-B model on male and tested it on female and vice-versa. When trained and tested within the same sex the prediction performance of the ensemble model was similar: AUC=0.88 (0.82-0.92) and 0.90 (0.85-0.94) for male and female, respectively. However, the overall performance dropped by 9% (0.79 (0.75-0.85)) and 8% (0.82 (0.77-0.88)) for male and female, respectively during cross training and testing.

Model

In recent years, there is a growing interest in developing EEG-based level of sedation monitors. However, among several unresolved important questions, it was not clear why these monitors failed to perform across different anesthetic drugs and patient groups. Using a large set of 44 QEEG features, the ensemble tree with bagging (ET-B) machine learning model achieved the best prediction performance of AUC>0.85 to discriminate between awake and sedated states. Thus, in some instances, this model can be used for a drug-independent nonlinear machine learning based sedation level prediction system. In some instances, individual features and/or features derived from spectral domain are not sufficient for real-time sedation level prediction at population level. Further, in some instances, addition of remifentanil affects the prediction performance of different features. Moreover, in some aspects, it is important to include all age groups and sex to develop a robust patient-independent sedation level monitoring system.

Figure 11:
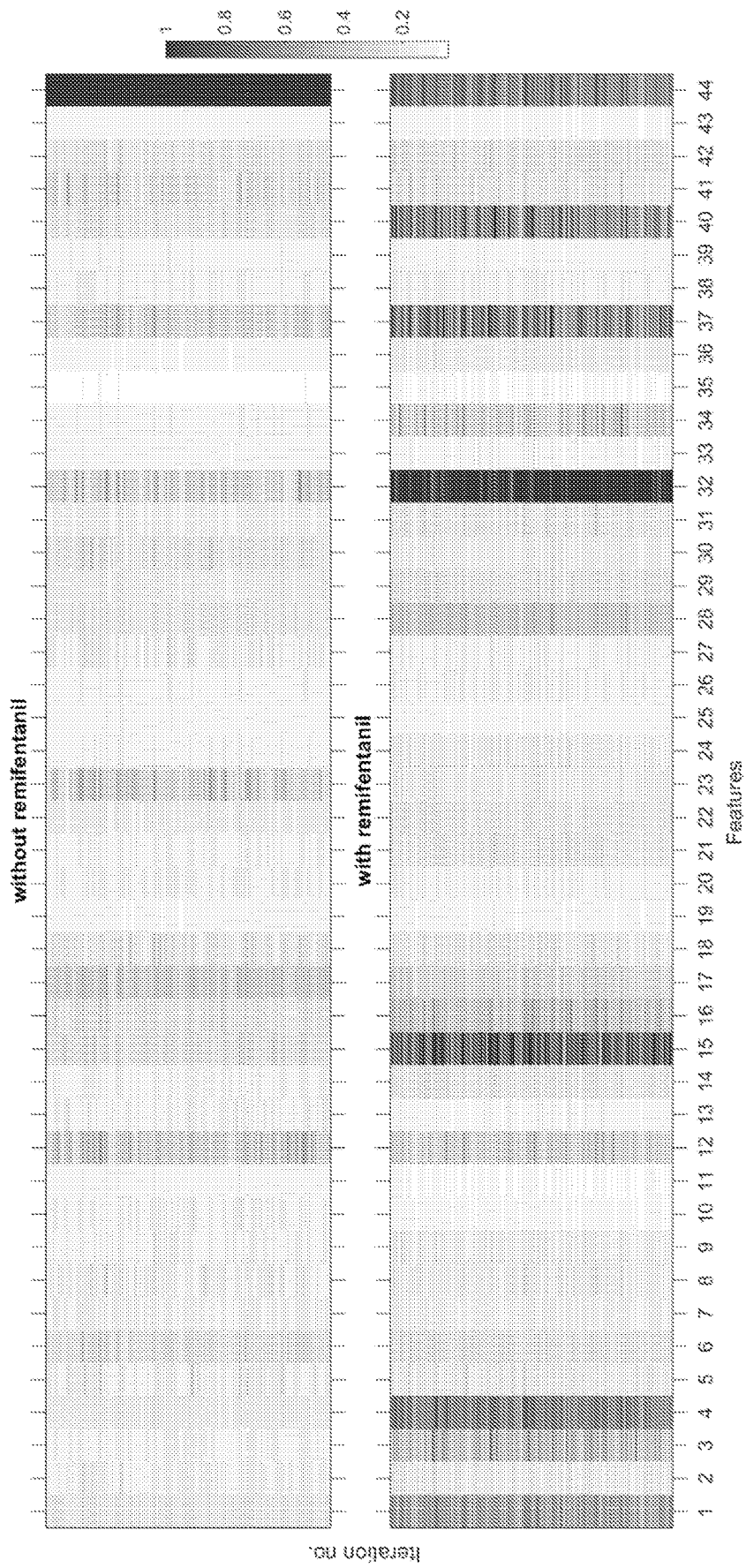
FIG. 11 shows effect of adding remifentanil to the predictive ability.

The EEG is the only technique available to accurately monitor sedation levels in real-time. One of the issues in developing EEG based sedation level monitors is the "feature engineering": which features should be used to accurately predict sedation states? Current EEG based sedation level monitors either use a single feature or few expert defined spectral features to predict sedation levels. Additionally, the addition of remifentanil significantly decreased the predictive ability of all features as shown in FIG. 11. Accordingly, in some instances, a multidimensional approach together with nonlinear machine learning algorithms can be used by the controller 1400 to generate a robust sedation index and determine which features to use based on the analysis discussed herein.

Except for tree based methods, the performance of all other machine learning models was significantly influenced by the addition of remifentanil. ET-B is an ensemble algorithm that develops a predictive model by combining multiple decisions to decrease bias/variance via bagging or bootstrap aggregation. A highly robust predictive decision is obtained by majority voting of decisions from individual classifiers in each ensemble. The ET-B algorithm selected a different combination of features to differentiate between awake and sedated states. Only four features: BSR, standard deviation of FM, SVDE and FD were commonly selected in all conditions making it an important feature to predict sedation levels. It should be noted that only two features from the spectral domain (power in alpha band and power in beta band) were selected by the ET-B algorithm suggesting that features derived from the traditional spectral analysis alone are not sufficient to track sedation levels.

Accordingly, by pooling data from different drugs, age and sex groups, it is possible to develop a robust realtime sedation level prediction system using advanced nonlinear machine learning algorithms. Features derived from traditional spectrogram alone may not be sufficient to accurately predict levels of sedation.

J. EEG Hardware System

FIG. 12 illustrates a block diagram of an EEG hardware system 1200, such as Masimo Sedline discussed above. The EEG hardware system 1200 can include an EEG sensor 1210 with multiple EEG electrodes. In the illustrated embodiment, the EEG sensor 1210 includes 6 electrodes, L1, L2, R1, R2, ground, and reference. The EEG sensor 1210 including the electrodes can be combined as a sensor package 1210 as shown in FIG. 13.

The EEG hardware system 1200 can include an EEG-adaptor cable 1220 for carrying the electrical signals from the EEG sensor 1210 to an adaptor 1230. The EEG adaptor cable 1220 can include an interface 1302 as shown in FIG. 3. The interface 1302 can be reusable and can removable connect mechanically and electrically to the EEG sensor 1210 (which may be disposable in some embodiments).

The EEG hardware system 1200 can include an adaptor 1230 for interfacing with both the EEG sensor 1210 and a patient monitor 1250. The adaptor 1230 can be a hardware module including circuits and other hardware components for processing EEG signals. In an embodiment, the adaptor 1230 can include one or more hardware processors 1232, a memory 1234, and power electronics 1236. The hardware processor 1232 can be programmed to implement the processes described herein for analyzing EEG signals. The memory 1234 can store instructions that can be executed by the hardware processor 1232. The memory 1234 can also store system parameters, including predetermined thresholds and conditions. The power electronics 1236 can include circuits for analog to digital conversion. The power electronics 1236 can also include filter circuitry for processing EEG signals. Some of the filters are stored as executable instructions and can be executed by the hardware processor 1232. The adaptor 1230 can generate outputs based on the received EEG signals and transmit the generated output to the patient monitor 1250. In some embodiments, the hardware processor 1252 of the patient monitor 1250 does not need to process any of the EEG signals. The patient monitor 1250 can receive the generated output for display or calculation of other health parameters. The adaptor 1230 and the patient monitor 1250 can be coupled with the adaptor-monitor cable 1240. The adaptor-monitor cable 1240 can include an interface 1304 as shown in FIG. 13 to connect to the patient monitor 1250. In some embodiments, the EEG hardware system 1200 does not include an adaptor 1230 and the EEG adaptor cable 1220 can directly connect to a patient monitor 1250. The patient monitor 1250 can process the EEG signals and execute processes described herein instead of the adaptor. In some embodiments, the hardware processor 1252 of the patient monitor 1250 can process the EEG signals and execute processes described herein in combination with the adaptor 1230.

The patient monitor 1250 can be a multi-parameter patient monitor for processing and analyzing sensor signals. The patient monitor 1250 includes one or more hardware processors 1252, a memory 1254, a display 1256, and power electronics 1258. The hardware processors 1252 of the patient monitor can be programmed to execute instructions stored in either an onboard memory of the adapter 1234 or the memory 1254 of the patient monitor. The patient monitor 1250 can also include a display 1256 that can display health parameters and graphs generated from the analysis of the received raw EEG signals or signals processed by the adaptor 1220.

FIG. 13 illustrates an embodiment of the EEG hardware system 1200 including the sensor 1210, adaptor 1230, the EEG-adaptor cable 1220, and the adaptor-monitor cable 1240. In an embodiment, sensor 1210 includes the L1 electrode, the L2 electrode, the R1 electrode, the R2 electrode, the reference electrode, and the ground electrode. The patient monitor 1250 is not shown in the illustrated figure.

FIG. 14 illustrates an embodiment of a controller 1400 for processing EEG signals captured from multiple channels corresponding to the electrodes of the EEG sensor 1210 attached to a patient. The controller 1400 can include one or more engines for processing, analyzing, and transforming the EEG signals into outputs that are readable by a clinician as illustrated in FIG. 4 and described below. The engines and other aspects of the controller 1400 can include programmed instructions capable of being executed on the one or more hardware processors 1252 and/or 1232 as shown in FIG. 12. The programmed instructions can be stored in a memory. The programmed instructions can correspond to the processes described herein. The engines and other aspects of the controller 1400 may also be implemented in a combination of hardware, such as circuits, FPGA, ASICs and the like and programmed instructions. In some embodiments, the controller 1400 operates the engines in parallel on the one or more hardware processors.

The controller 1400 can include a signal collection engine 1410 for collecting and storing EEG signals in a memory. In an embodiment, the signal collection engine 1410 can store a circular buffer of EEG signals in a memory, which can refer to the memory 1234 or 1254 or a combination. The circular buffer can be 1.2 seconds. In other embodiments, the circular buffer can be more than 1.2 seconds, such as 2.4 seconds, 5 seconds, 10 seconds or more. Yet, in other embodiments, the circular buffer can be less than 1.2 seconds.

The controller 1400 can also include a display engine 1404. The display engine 1404 can generate a user interface for displaying the DSA on a display 1256 of the patient monitor 1250. In an embodiment, the display engine displays a state of sedation for the patient as determined above by the machine learning models. The display engine 1404 can also generate graphs and health parameters for display based on the determined state of sedation.

In some instances, the controller 1400 can include a Feature Extraction Engine 1412 to extract the QEEG features (as shown in Table 1 above) from the EEG signals.

As discussed herein, the terms "sedation level", "patient state indicator", and "sedation index" and the like are used interchangeably and refer to an indicia of measurement that is measured and tracked internally by the controller 1400. The patient state indicator can be a numerical value, a textual description, a color indicator, or the like. In an embodiment, the patient state indicator is based on a numerical scale from 0 to 100, where 100 would represent an awake state and a lower number would indicate that a patient is likely in one of the sedated states. The patient state indicator may also be a textual description indicating that the patient is awake, in light sedation, moderate sedation, deep sedation, or the like. One of ordinary skill in the art will understand that in some embodiments, the patient state indicator may be expressed as both a numerical indicator and as a textual description and/or the like at the same time. One of ordinary skill in the art will also understand that a patient state indicator or sedation index that is expressed as a numerical value can be converted to a textual description, color indicator, or the like. The patient state indicator or sedation index can provide a measure for the state of consciousness of a patient. The models described above provide rules for improving the automatic determining of the patient state indicator. For example, in some instances, certain machine learning models were found to provide a better estimate (as discussed above. Moreover, certain features were also found to provide a better estimate across a diverse cross-section. The rules improve the correlation between the patient state indicator and the physiological state of the patient. Accordingly, caregivers can use the patient state indicator to guide them while treating a patient undergoing anesthesia. For example, if the indicator shows that the patient is coming out of anesthesia prematurely, the anesthesiologist can increase dosage. Furthermore, the anesthesiologist can also use the index to monitor and deliver the sedative drug. Accordingly, the models described above improve the determination of sedation index and correspondingly improve the field of medicine and the treatment provided to a patient.

K. Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both as discussed above.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method for generating a sedation level estimate, the method comprising:
   receiving an electroencephalography (EEG) signal from a sensor electrode attached to a patient, the EEG signal comprising a plurality of channels;
   segmenting the EEG signal into smaller epochs for each channel;
   extracting features of the EEG signal in each epoch, the features comprising time domain features, frequency domain features, and entropy domain features;
   determining a median of features among the plurality of channels for each epoch;
   determining, by a classifier, a probabilistic estimate of a patient sedation, wherein the classifier is trained using training data comprising MOAA/S scores, the training data selected to exclude MOAA/S scores in a center range of the MOAA/S scores;

generating, using a determined correlation, a sedation level estimate, the sedation level estimate comprising a continuous sedation score; and displaying an indication of the sedation level estimate.

2. The method of claim 1, wherein an epoch comprises 4 seconds.

3. The method of claim 1, wherein the features comprise quantitative electroencephalogram (QEEG) features.

4. The method of claim 3, wherein extracting features comprises extracting at least 44 QEEG features.

5. The method of claim 1, wherein classifier comprises a binary classifier trained by machine learning.

6. The method of claim 5, wherein the binary classifier is trained using awake and sedated epoch data, the awake and sedated epoch data comprising a plurality of epochs having sedation scores.

7. The method of claim 1, wherein the determined correlation comprises a correlation between the probabilistic estimate of the patient sedation and a sedation score.

8. The method of claim 1, wherein the center range comprises MOAA/S scores of 2 or 3.

* * * * *